(12) United States Patent
Kuo et al.

(10) Patent No.: US 8,501,240 B2
(45) Date of Patent: *Aug. 6, 2013

(54) COMPOSITIONS COMPRISING AN ACTIVE AGENT

(75) Inventors: Mei-chang Kuo, Palo Alto, CA (US); David Lechuga-Ballesteros, San Jose, CA (US)

(73) Assignee: Novartis AG, Basel (CH)

(*) Notice: Subject to any disclaimer, the term of this patent is extended or adjusted under 35 U.S.C. 154(b) by 0 days.

This patent is subject to a terminal disclaimer.

(21) Appl. No.: 12/343,365

(22) Filed: Dec. 23, 2008

(65) Prior Publication Data

US 2009/0117193 A1  May 7, 2009

Related U.S. Application Data

(60) Division of application No. 10/985,509, filed on Nov. 10, 2004, now Pat. No. 7,482,024, which is a continuation of application No. 10/313,343, filed on Dec. 6, 2002, now Pat. No. 6,835,372, which is a continuation of application No. 09/548,759, filed on Apr. 13, 2000, now Pat. No. 6,518,239.

(60) Provisional application No. 60/162,451, filed on Oct. 29, 1999, provisional application No. 60/164,236, filed on Nov. 8, 1999, provisional application No. 60/172,769, filed on Dec. 20, 1999, provisional application No. 60/178,383, filed on Jan. 27, 2000, provisional application No. 60/178,415, filed on Jan. 27, 2000.

(51) Int. Cl.
*A61K 9/14* (2006.01)
*A61K 38/05* (2006.01)
*A61K 38/06* (2006.01)

(52) U.S. Cl.
USPC ........ 424/499; 424/489; 514/21.9; 514/21.91

(58) Field of Classification Search
None
See application file for complete search history.

(56) References Cited

U.S. PATENT DOCUMENTS

| | | | |
|---|---|---|---|
| 3,906,950 A | 9/1975 | Cocozza | |
| 4,013,075 A | 3/1977 | Cocozza | |
| 4,476,120 A | 10/1984 | Gonella | |
| 4,667,668 A | 5/1987 | Wetterlin | |
| 4,668,218 A | 5/1987 | Virtanen | |
| 4,668,281 A | 5/1987 | Levitt | |
| 4,805,811 A | 2/1989 | Wetterlin | |
| 4,818,542 A | 4/1989 | DeLuca et al. | |
| 5,059,587 A | 10/1991 | Yamamoto et al. | |
| 5,182,258 A | 1/1993 | Chiou | |
| 5,290,929 A | 3/1994 | Koster et al. | |
| 5,320,094 A | 6/1994 | Laube et al. | |
| 5,376,386 A | 12/1994 | Ganderton et al. | |
| 5,388,572 A | 2/1995 | Mulhauser et al. | |
| 5,389,379 A | 2/1995 | Dirix et al. | |
| 5,458,135 A | 10/1995 | Patton et al. | |
| 5,519,049 A | 5/1996 | Norris et al. | |
| 5,522,385 A | 6/1996 | Lloyd et al. | |
| 5,654,007 A | 8/1997 | Johnson et al. | |
| 5,663,198 A | 9/1997 | Reul et al. | |
| 5,672,581 A | 9/1997 | Rubsamen et al. | |
| 5,740,794 A | 4/1998 | Smith et al. | |
| 5,767,068 A | 6/1998 | VanDevanter et al. | |
| 5,775,320 A | 7/1998 | Patton et al. | |
| 5,785,049 A | 7/1998 | Smith et al. | |
| 5,826,633 A | 10/1998 | Parks et al. | |
| 5,855,913 A | 1/1999 | Hanes et al. | |
| 5,875,776 A | 3/1999 | Vaghefi | |
| 5,908,639 A | 6/1999 | Simpkin et al. | |
| 5,922,675 A | 7/1999 | Baker et al. | |
| 5,976,574 A | 11/1999 | Gordon | |
| 5,985,248 A | 11/1999 | Gordon et al. | |
| 5,985,309 A | 11/1999 | Edwards et al. | |
| 6,001,336 A | 12/1999 | Gordon | |
| 6,089,228 A | 7/2000 | Smith et al. | |
| 6,257,233 B1 | 7/2001 | Burr et al. | |
| 6,518,239 B1 * | 2/2003 | Kuo et al. | 514/2 |
| 6,835,372 B2 * | 12/2004 | Kuo et al. | 424/9.34 |
| 7,112,341 B1 | 9/2006 | Nagarajan et al. | |
| 7,223,554 B2 | 5/2007 | Garrett et al. | |
| 7,482,024 B2 * | 1/2009 | Kuo et al. | 424/499 |
| 2003/0138402 A1 | 7/2003 | Yamashita et al. | |
| 2005/0147567 A1 | 7/2005 | Kuo et al. | |

FOREIGN PATENT DOCUMENTS

| | | |
|---|---|---|
| EP | 0129985 | 1/1985 |
| EP | 0467172 | 1/1992 |
| EP | 0 869 816 | 10/1998 |
| WO | WO 9013328 | 11/1990 |
| WO | WO 9404148 | 3/1994 |
| WO | WO 9509616 | 4/1995 |
| WO | WO 9531479 | 11/1995 |
| WO | WO 9609085 | 3/1996 |
| WO | WO 96/21461 | * 7/1996 |
| WO | WO 9621461 | 7/1996 |
| WO | WO 9632096 | 10/1996 |
| WO | WO 9632149 | 10/1996 |
| WO | WO 97/03649 | 2/1997 |
| WO | WO 9703649 | 2/1997 |
| WO | WO 9723239 | 7/1997 |

(Continued)

OTHER PUBLICATIONS

Colthorpe et al (Pharmaceutical Research 12:356-359, 1995).*

(Continued)

*Primary Examiner* — Mary E Mosher
(74) *Attorney, Agent, or Firm* — Janah & Associates, P.C.

(57) ABSTRACT

The present invention provides a highly dispersible formulation comprising an active agent and a dipeptide or tripeptide comprising at least two leucyl residues. The composition of the invention possesses superior aerosol properties and is thus preferred for aerosolized administration to the lung. Also provided are a method for (i) increasing the dispersibility of an active-agent containing formulation for administration to the lung, and (ii) delivery of the composition to the lungs of a subject.

39 Claims, No Drawings

FOREIGN PATENT DOCUMENTS

| | | |
|---|---|---|
| WO | WO 9741031 | 11/1997 |
| WO | WO 9741833 | 11/1997 |
| WO | WO 9816205 | 4/1998 |
| WO | WO 9829096 | 7/1998 |
| WO | WO 0061178 | 10/2000 |
| WO | WO 0132144 | 5/2001 |

OTHER PUBLICATIONS

Maa et al (Journal of Pharmaceutical Sciences 87:152-159, 1998).*

Møller et al (Clinical Endocrinology 40:511-513, 1994).*

Baldwin Dr et al "Azithromycin concentrations at the sites of pulmonary infection" Eur Respir J 3:886 (1990).

Conte John E Jr et al "Single-Dose Intrapulmonary Pharmacokinetics of Azithromycin, Clarithromycin, Ciprofloxacin, and Cefuroxime in Volunteer Subjects" Antimicrob Agents Chemother 40(7):1617 (1996).

Cook Peter J et al "Concentrations of OPC-17116, a new fluoroquinolone antibacterial, in serum and lung compartments" J Antimicrob Chemother 35:317 (1995).

Kobayashi Motomasa et al "Marine Natural Products. XXXI. Structure-Activity Correlation of a Potent Cytotoxic Dimeric Macrolide Swinholide A, from the Okinawan Marine Sponge *Theonella swinhoei*, and Its Isomers" Chem Pharm Bull 42(1)19 (1994).

Murata Mitsuo et al "Carrier-Mediated Lung Distribution of HSR-903, a New Quinolone Antibacterial Agent" J Pharmacol Exp Ther 289(1):79 (1999) 1:1.

Olsen Keith M et el "Intrapulmonary Pharmacokinetics of Azithromycin in Healthy Volunteers Given Five Oral Doses" Antimicrob Agents Chemother 40(11):2582 (1996).

Patel Kalpana B et al "Comparison of Bronchopulmonary Pharmacokinetics of Clarithromycin and Azithromycin" Antimicrob Agents Chemother 40(10):2375 (1996).

Sato Masahiko et al "Biosynthetic Human Parathryoid Hormone (1-34) Effects on Bone Quality in Aged Ovariectomized Rats" Endocrinology 138(10):4330 (1997).

Sutcliffe Joyce et al "*Streptococcus pneumoniae* and *Streptococcus pyogenes* Resistant to Macrolides but Sensitive to Clindamycin: a Common Resistance Pattern Mediated by an Efflux System" Antimicrob Agents Chemother 40(8):1817 (1996).

International Search Report, PCT/US00/09785 (Nov. 30, 2000).

Written Opinion, PCT/US00/09785 (Aug. 28, 2001).

Bibliographic data: EP 0472598 (Mar. 4, 1992).

Bibliographic data: EP 0869816 (Oct. 14, 1998).

Bibliographic data: EP 1223915 (Jul. 24, 2002).

* cited by examiner

COMPOSITIONS COMPRISING AN ACTIVE AGENT

This application is a divisional of U.S. patent application Ser. No. 10/985,509 filed on Nov. 10, 2004, now U.S. Pat. No. 7,482,024, which is a continuation of U.S. patent application Ser. No. 10/313,343 filed on Dec. 6, 2002, now U.S. Pat. No. 6,835,372, which is a continuation of U.S. patent application Ser. No. 09/548,759 filed on Apr. 13, 2000, now U.S. Pat. No. 6,518,239. This application claims the benefit of priority of the following U.S. Provisional Patent Applications: Ser. No. 60/162,451 filed on Oct. 29, 1999; Ser. No. 60/164,236 filed on Nov. 8, 1999; Ser. No. 60/172,769 filed on Dec. 20, 1999; Ser. No. 60/178,383 filed on Jan. 27, 2000; and Ser. No. 60/178,415 filed on Jan. 27, 2000, all of which are incorporated herein by reference in their entirety.

FIELD OF THE INVENTION

The present invention is directed to highly dispersive dry powder compositions, and in particular, to highly dispersive, inhalable dry powder compositions for aerosolized delivery to the lungs. The dry powders of the invention contain an active agent and a di- or tripeptide containing at least 2 leucyl residues, and are physically and chemically stable upon storage. The powders of the invention also demonstrate superior aerosol performance.

BACKGROUND OF THE INVENTION

Traditionally, inhalation therapy has played a relatively minor role in the administration of biotherapeutics and conventional pharmaceuticals when compared to more traditional drug administration routes, such as oral and intravenous. Injection is the customary route of delivery of biotherapeutics (e.g., peptides, proteins and nucleic acids), and due to the many drawbacks associated with injection (e.g., inconvenience, discomfort, patient aversion to needle-based delivery methods), alternative administration routes are needed.

Pulmonary delivery is one such alternative administration route which can offer several advantages over subcutaneous administration. These advantages include the convenience of patient self-administration, the potential for reduced drug side-effects, ease of delivery by inhalation, the elimination of needles, and the like. Many preclinical and clinical studies with inhaled proteins, peptides, DNA and small molecules have demonstrated that efficacy can be achieved both within the lungs and systemically. However, despite such results, the role of inhalation therapy in the health care field has not grown as expected over recent years, in part due to a set of problems unique to the development of inhalable drug formulations. Dry powder formulations, while offering unique advantages over cumbersome liquid dosage forms and propellant-driven formulations, are prone to aggregation and low flowability phenomena which considerably diminish the efficiency of dry powder-based inhalation therapies.

Particulate aggregation, caused by particle-particle interactions, such as hydrophobic, electrostatic, and capillary interactions, must be minimized in order to provide dispersible powders for effective inhalation therapies. Various approaches have been utilized in efforts to prepare dry powders having minimal particle aggregation and good aerosol properties. These approaches include the modification of dry powder particle surface texture (Ganderton, et al., U.S. Pat. No. 5,376,386), the co-delivery of large carrier particles (absent drug) with therapeutic aerosols to achieve efficient aerosolization, particle coatings (Hanes, U.S. Pat. No. 5,855,913; Ruel, et al., U.S. Pat. No. 5,663,198) aerodynamically light particles (Edwards, et al., U.S. Pat. No. 5,985,309), use of antistatic agents, (Simpkin, et al., U.S. Pat. No. 5,908,639) and the addition of certain excipients, e.g., surfactants (Hanes U.S. Pat. No. 5,855,913; Edwards, U.S. Pat. No. 5,985,309). Unfortunately, the formation of particulate aggregates and production of powders having poor flow properties and low dispersivities continue to plague development efforts to prepare aerosolizable dry powders for inhalation therapy. Thus, a need exists for improved inhalable aerosols for the pulmonary delivery of therapeutic agents, and in particular, for dry powders having excellent aerosol properties and reduced particle-particle interactions, irrespective of the therapeutic agent.

SUMMARY OF THE INVENTION

The present invention is based upon the discovery of a particular class of excipients, which, when incorporated into dry powder formulations for aerosolization and delivery to the lung, notably improves the dispersivity and aerosolization properties of the dry powders, irrespective of the type of active agent contained in the formulation. More particularly, the invention provides a dry powder composition which comprises an active agent and a di or tri-peptide comprising at least two leucines. Preferred di- and tripeptides are those which are surface active.

The dry powder of the invention typically contains from about 2% by weight to about 99% by weight di- or tri-peptide, and may optionally contain additional excipients or carriers, such as carbohydrates, amino acids, peptides, proteins, organic acid salts, and/or polymers.

The presence of the di- or tri-peptide is effective to notably increase the emitted dose of the dry powder over the emitted dose of the powder composition absent the di- or tri-peptide. In one particular embodiment of the invention, the dry to powder of the invention is characterized by an emitted dose of at least about 30%. In another embodiment, the concentration of the dileucyl-di- or tri-peptide on the surface of the particles is greater than in the bulk powder.

Additional features of the dry powder particles of the invention include, in one embodiment, a mass median diameter of less than about 10 microns, and in yet another embodiment, a mass median aerodynamic diameter of less than about 10 microns. In yet another embodiment, the dry powder comprises particles having a bulk density from 0.1 to 10 grams per cubic centimeter.

The dry powder of the invention is further characterized by both physical and chemical stability upon storage, as characterized, in one embodiment, by a drop in emitted dose of no more than about 10% when stored under ambient conditions for a period of three months. In another embodiment, the chemical stability of the dry powder is characterized by degradation of less than about 5% by weight of the active agent upon storage of the dry powdered composition under ambient conditions for a period of three months.

In another aspect, the invention provides a method for enhancing the aerosol performance of a dry powder. In the method, a di- or tri-peptide is incorporated into an active-agent containing liquid formulation. The resulting liquid formulation is dried to produce a dry powder containing the active agent and the di- and/or tripeptide, whereby the resultant dry powder possesses an emitted dose that is increased over the emitted dose of a dry powder having the same components but absent the di- or tripeptide.

In one embodiment of the method, the liquid formulation is an aqueous formulation. In another particular embodiment of the method, the liquid formulation is spray-dried to produce a dry powder.

In yet a further aspect, the invention provides a method for increasing the aerosol performance of an active-agent containing formulation suitable for administration to the lung. According to the method, a di- or tripeptide comprising at least two leucines is incorporated into a formulation comprising an active agent. The resulting composition comprising the active agent and the di- or tripeptide possesses an emitted dose that is increased over the emitted dose of a composition having the same components but absent the di- or tripeptide. In one embodiment, the method results in a liquid composition suitable for aerosolized administration to the lung; in an alternative embodiment, the method results in a dry powdered composition suitable for aerosolized administration to the lung.

Yet another aspect of the invention is directed to a method for delivery of a dry powder composition to the lungs of a mammalian subject by administering by inhalation the compositions of the invention as previously described, in aerosolized form.

These and other objects and features of the invention will become more fully apparent when the following detailed description is read in conjunction with the accompanying figures and examples.

DETAILED DESCRIPTION OF THE INVENTION

I. Definitions

The following terms as used herein have the meanings indicated.

"Active agent" as described herein includes any agent, drug, compound, composition of matter or mixture which provides some pharmacologic, often beneficial, effect that can be demonstrated in-vivo or in vitro. This includes foods, food supplements, nutrients, nutriceuticals, drugs, vaccines, antibodies, vitamins, and other beneficial agents. As used herein, these terms further include any physiologically or pharmacologically active substance that produces a localized or systemic effect in a patient.

"Amino acid" refers to any compound containing both an amino group and a carboxylic acid group. Although the amino group most commonly occurs at the position adjacent to the carboxy function, the amino group may be positioned at any location within the molecule. The amino acid may also contain additional functional groups, such as amino, thio, carboxyl, carboxamide, imidazole, etc. An amino acid may be synthetic or naturally occurring, and may be used in either its racemic or optically active (D-, or L-) form.

"Leucine", whether present as a single amino acid or as an amino acid component of a peptide, refers to the amino acid leucine, which may be a racemic mixture or in either its D- or L-form, as well as modified forms of leucine (i.e., where one or more atoms of leucine have been substituted with another atom or functional group) in which the dispersibility-enhancing effect of the modified amino acid or peptide is substantially unchanged or unimproved over that of the unmodified material.

"Dipeptide", also referred to herein as a dimer, refers to a peptide composed of two amino acids.

"Tripeptide", also referred to herein as a trimer, refers to a peptide composed of three amino acids.

A "surface active" material is one having surface activity (measured, e.g., by surface tensiometry), as characterized by its ability to reduce the surface tension of the liquid in which it is dissolved. Surface tension, which is associated with the interface between a liquid and another phase, is that property of a liquid by virtue of which the surface molecules exhibit an inward attraction.

Typically, in the context of the present invention, a surface active dipeptide or tripeptide is identified by preparing solutions of varying concentrations (from approximately 0.01% wt/vol (0.1 mg/ml) to approximately 2% wt/vol (20 mg/ml) of the subject peptide in water, and measuring the surface tension of each of the solutions. A surface-active peptide is one which, when present at any concentration in solution, though typically present in an amount greater than 0.25 mg/ml, is effective to lower the surface tension of water from its control value. A peptide that is more surface active than another peptide is one which decreases the surface tension of water to a greater extent, when present in the liquid at the same concentration and measured under the same set of experimental conditions.

"Dry powder" refers to a powder composition that typically contains less than about 20% moisture, preferably less than 10% moisture, more preferably contains less than about 5-6% moisture, and most preferably contains less than about 3% moisture, depending upon the particular formulation.

A dry powder that is "suitable for pulmonary delivery" refers to a composition comprising solid (i.e., non-liquid) or partially solid particles that are capable of being (i) readily dispersed in/by an inhalation device and (ii) inhaled by a subject so that a portion of the particles reach the lungs to permit penetration into the alveoli. Such a powder is considered to be "respirable".

"Aerosolized" or "aerosolizable" particles are particles which, when dispensed into a gas stream by either a passive or an active inhalation device, remain suspended in the gas for an amount of time sufficient for at least a portion of the particles to be inhaled by the patient, so that a portion of the particles reaches the lungs.

"Emitted Dose" or "ED" provides an indication of the delivery of a drug formulation from a suitable inhaler device after a firing or dispersion event. More specifically, for dry powder formulations, the ED is a measure of the percentage of powder which is drawn out of a unit dose package and which exits the mouthpiece of an inhaler device. The ED is defined as the ratio of the dose delivered by an inhaler device to the nominal dose (i.e., the mass of powder per unit dose placed into a suitable inhaler device prior to firing). The ED is an experimentally-determined parameter, and is typically determined using an in-vitro device set up which mimics patient dosing. To determine an ED value, a nominal dose of dry powder, typically in unit dose form, is placed into a suitable dry powder inhaler (such as that described in U.S. Pat. No. 5,785,049, assigned to Inhale Therapeutic Systems) which is then actuated, dispersing the powder. The resulting aerosol cloud is then drawn by vacuum from the device, where it is captured on a tared filter attached to the device mouthpiece. The amount of powder that reaches the filter constitutes the emitted dose. For example, for a 5 mg dry powder-containing dosage form placed into an inhalation device, if dispersion of the powder results in the recovery of 4 mg of powder on a tared filter as described above, then the emitted dose for the dry powder composition is: 4 mg (delivered dose)/5 mg (nominal dose)×100=80%. For non-homogenous powders, ED values provide an indication of the delivery of drug from an inhaler device after firing rather than of dry powder, and are based on amount of drug rather than on total powder weight. Similarly for MDI and nebulizer dosage forms, the ED corresponds to the percentage of drug which is drawn from a dosage form and which exits the mouthpiece of an inhaler device.

"Fine particle dose" or "FPD" is defined as the mass percent of powder particles having an aerodynamic diameter less than 3.3 μm, typically determined by to measurement in an Andersen cascade impactor. This parameter provides an indication of the percent of particles having the greatest potential to reach the deep lung of a patient for systemic uptake of a drug substance.

A "dispersible" or "dispersive" powder is one having an ED value of at least about 30%, more preferably 40-50%, and even more preferably at least about 50-60%.

"Mass median diameter" or "MMD" is a measure of mean particle size, since the powders of the invention are generally polydisperse (i.e., consist of a range of particle sizes). MMD values as reported herein are determined by centrifugal sedimentation, although any number of commonly employed techniques can be used for measuring mean particle size (e.g., electron microscopy, light scattering, laser diffraction).

"Mass median aerodynamic diameter" or "MMAD" is a measure of the aerodynamic size of a dispersed particle. The aerodynamic diameter is used to describe an aerosolized powder in terms of its settling behavior, and is the diameter of a unit density sphere having the same settling velocity, in air, as the particle. The aerodynamic diameter encompasses particle shape, density and physical size of a particle. As used herein, MMAD refers to the midpoint or median of the aerodynamic particle size distribution of an aerosolized powder determined by cascade impaction, unless otherwise indicated.

"Pharmaceutically acceptable salt" includes, but is not limited to, salts prepared with inorganic acids, such as chloride, sulfate, phosphate, diphosphate, hydrobromide, and nitrate salts, or salts prepared with an organic acid, such as malate, maleate, fumarate, tartrate, succinate, ethylsuccinate, citrate, acetate, lactate, methanesulfonate, benzoate, ascorbate, para-toluenesulfonate, palmoate, salicylate and stearate, as well as estolate, gluceptate and lactobionate salts. Similarly, salts containing pharmaceutically acceptable cations include, but are not limited to, sodium, potassium, calcium, aluminum, lithium, and ammonium (including alkyl substituted ammonium).

"Pharmaceutically acceptable excipient or carrier" refers to an excipient that may optionally be included in the compositions of the invention, and taken into the lungs with no significant adverse toxicological effects to the subject, and particularly to the lungs of the subject.

"Pharmacologically effective amount" or "physiologically effective amount of a bioactive agent" is the amount of an active agent present in an aerosolizable composition as described herein that is needed to provide a desired level of active agent in the bloodstream or at the site of action (e.g., the lungs) of a subject to be treated to give an anticipated physiological response when such composition is administered pulmonarily. The precise amount will depend upon numerous factors, e.g., the active agent, the activity of the composition, the delivery device employed, the physical characteristics of the composition, intended patient use (i.e., the number of doses administered per day), patient considerations, and the like, and can readily be determined by one skilled in the art, based upon the information provided herein.

"Polymer" refers to a high molecular weight polymeric compound or macromolecule built by the repitition of small, simple chemical units. A polymer may be a biological polymer, i.e., is naturally occurring (e.g., proteins, carbohydrates, nucleic acids) or a non-biological, synthetically-produced polymer (e.g., polyethylene glycols, polyvinylpyrrolidones, Ficolls, and the like), as well known in the art.

II. The Composition

The present invention is based upon the Applicants' discovery of a class of compounds, dipeptides and tripeptides containing two or more leucines, which when incorporated into formulations for administration to the lung, impart superior aerosol properties to the resulting formulations. Moreover, the Applicants have discovered, surprisingly that, these di- and tripeptides are effective to significantly enhance the dispersibility of the resulting formulations, irrespective of the type of active agent present in the formulation. Thus, these di- and tripeptides can be employed in a wide variety of formulations, to increase the aerosol performance of the resulting compositions, and in some cases, to provide aerosolizable formulations in situations where an aerosolizable formulation was previously unknown or unattainable. The present invention, although directed in certain respects to dry powder formulations, is meant to encompass liquid formulations as well. The components of the formulations of the invention will now be described.

A. The Active Agent

An active agent for incorporation in the compositions described herein may be an inorganic or an organic compound, including, without limitation, drugs which act on: the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system, and the central nervous system. Suitable agents may be selected from, for example, hypnotics and sedatives, psychic energizers, tranquilizers, respiratory drugs, anticonvulsants, muscle relaxants, antiparkinson agents (dopamine antagonists), analgesics, anti-inflammatories, antianxiety drugs (anxiolytics), appetite suppressants, antimigraine agents, muscle contractants, anti-infectives (antibiotics, antivirals, antifungals, vaccines) antiarthritics, antimalarials, antiemetics, anepileptics, bronchodilators, cytokines, growth factors, anti-cancer agents, antithrombotic agents, antihypertensives, cardiovascular drugs, antiarrhythmics, antioxicants, anti-asthma agents, hormonal agents including contraceptives, sympathomimetics, diuretics, lipid regulating agents, antiandrogenic agents, antiparasitics, anticoagulants, neoplastics, antineoplastics, hypoglycemics, nutritional agents and supplements, growth supplements, antienteritis agents, vaccines, antibodies, diagnostic agents, and contrasting agents. The active agent, when administered by inhalation, may act locally or systemically.

The active agent may fall into one of a number of structural classes, including but not limited to small molecules, peptides, polypeptides, proteins, polysaccharides, steroids, proteins capable of eliciting physiological effects, nucleotides, oligonucleotides, polynucleotides, fats, electrolytes, and the like.

Examples of active agents suitable for use in this invention include but are not limited to calcitonin, erythropoietin (EPO), Factor VIII, Factor IX, ceredase, cerezyme, cyclosporin, granulocyte colony stimulating factor (GCSF), thrombopoietin (TPO), alpha-1 proteinase inhibitor, elcatonin, granulocyte macrophage colony stimulating factor (GMCSF), growth hormone, human growth hormone (HGH), growth hormone releasing hormone (GHRH), heparin, low molecular weight heparin (LMWH), interferon alpha, interferon beta, interferon gamma, interleukin-1 receptor, interleukin-2, interleukin-1 receptor antagonist, interleukin-3, interleukin-4, interleukin-6, luteinizing hormone releasing hormone (LHRH), factor IX insulin, pro-insulin, insulin analogues (e.g., mono-acylated insulin as described in U.S. Pat. No. 5,922,675), amylin, C-peptide, somatostatin, somatostatin analogs including octreotide, vasopressin, follicle stimulating hormone (FSH), insulin-like growth factor (IGF), insulintropin, macrophage colony stimulating factor (M-CSF), nerve growth factor (NGF), tissue growth factors, keratinocyte growth factor (KGF), glial growth factor (GGF), tumor necrosis factor (TNF), endothelial growth factors, parathyroid hormone (PTH), glucagon-like peptide thymosin alpha 1, IIb/IIIa inhibitor, alpha-1 antitrypsin, phosphodiesterase (PDE) compounds, VLA-4 inhibitors, bisphosphonates, respiratory syncytial virus antibody, cystic fibrosis transmembrane regulator (CFTR) gene, deoxyreibonuclease (Dnase), bactericidal/permeability increasing protein (BPI), anti-CMV antibody, 13-cis retinoic acid, macrolides such as erythromycin, oleandomycin, troleandomycin, roxithromycin, clarithromycin, davercin, azithromycin, flurithromycin, dirithromycin, josamycin, spiromycin, midecamycin, leucomycin, miocamycin, rokitamycin, andazithromycin, and swinolide A; fluoroquinolones such as ciprofloxacin, ofloxacin, levofloxacin, trovafloxacin, alatrofloxacin, moxifloxicin, norfloxacin, enoxacin, grepafloxacin, gatifloxacin, lomefloxacin, sparfloxacin, temafloxacin, pefloxacin, amifloxacin, fleroxacin, tosutloxacin, prulifloxacin, irloxacin, pazufloxacin, clinafloxacin, and sitafloxacin, aminoglycosides such as gentamicin, netilmicin, paramecin, tobramycin, amikacin, kanamycin, neomycin, and streptomycin, vancomycin, teicoplanin, rampolanin, mideplanin, colistin, daptomycin, gramicidin, colistimethate, polymixins such as polymixin B, capreomycin, bacitracin, penems; penicillins including penicilinase-sensitive agents like penicillin G, penicillin V, penicilinase-resistant agents like methicillin, oxacillin, cloxacillin, dicloxacillin, floxacillin, nafcillin; gram negative microorganism active agents like ampicillin, amoxicillin, and hetacillin, cillin, and galampicillin; antipseudomonal penicillins like carbenicillin, ticarcillin, aziocillin, meziocillin, and piperacillin; cephalosporins like cefpodoxime, cefprozil, ceftbuten, ceftizoxime, ceftriaxone, cephalothin, cephapirin, cephalexin, cephradrine, cefoxitin, cefamandole, cefazolin, cephaloridine, cefaclor, cefadroxil, cephaloglycin, cefuroxime, ceforanide, cefotaxime, cefatrizine, cephacetrile, cefepime, cefixime, cefonicid, cefoperazone, cefotetan, cefinetazole, ceftazidime, loracarbef, and moxalactam, monobactams like aztreonam; and carbapenems such as imipenem, meropenem, pentamidine isethiouate, albuterol sulfate, lidocaine, metaproterenol sulfate, beclomethasone diprepionate, triamcinolone acetamide, budesonide acetonide, fluticasone, ipratropium bromide, flunisolide, cromolyn sodium, ergotamine tartrate and where applicable, analogues, agonists, antagonists, inhibitors, and pharmaceutically acceptable salt forms of the above. In reference to peptides and proteins, the invention is intended to encompass synthetic, native, glycosylated, unglycosylated, pegylated forms, and biologically active fragments and analogs thereof.

Active agents for use in the invention further include nucleic acids, as bare nucleic acid molecules, vectors, associated viral particles, plasmid DNA or RNA or other nucleic acid constructions of a type suitable for transfection or transformation of cells, i.e., suitable for gene therapy including antisense. Further, an active agent may comprise live attenuated or killed viruses suitable for use as vaccines. Other useful drugs include those listed within the Physician's Desk Reference (most recent edition).

The amount of active agent in the formulation will be that amount necessary to deliver a therapeutically effective amount of the active agent per unit dose to achieve the desired result. In practice, this will vary widely depending upon the particular agent, its activity, the severity of the condition to be treated, the patient population, dosing requirements, and the desired therapeutic effect. The composition will generally contain anywhere from about 1% by weight to about 99% by weight active agent, typically from about 2% to about 95% by weight active agent, and more typically from about 5% to 85% by weight active agent, and will also depend upon the relative amounts of additives contained in the composition. The compositions of the invention are particularly useful for active agents that are delivered in doses of from 0.001 mg/day to 100 mg/day, preferably in doses from 0.01 mg/day to 75 mg/day, and more preferably in doses from 0.10 mg/day to 50 mg/day.

It is to be understood that more than one active agent may be incorporated into the formulations described herein and that the use of the term "agent" in no way excludes the use of two or more such agents.

B. Dispersibility-Enhancing Peptides

Compositions of the invention will include one or more di- or tripeptides containing two or more leucine residues. As discussed above, the invention is based upon the Applicants' discovery that di-leucyl-containing dipeptides (e.g., dileucine) and tripeptides are superior in their ability to increase the dispersibility of powdered compositions, and, as demonstrated in the Examples, are unexpectedly better than leucine in improving aerosol performance.

Di-leucyl containing tripeptides for use in the invention are tripeptides having the formula, X-Y-Z, where at least X and Y or X and Z are leucyl residues (i.e., the leucyl residues can be adjacent to each other (at the 1 and 2 positions), or can form the ends of the trimer (occupying positions 1 and 3). The remaining amino acid contained in the trimer can be any amino acid as defined in section I above. Suitable are amino acids such as glycine (gly), alanine (ala), valine (val), leucine (leu), isoleucine (ile), methionine (met), proline (pro), phenylalanine (phe), trytophan (trp), serine (ser), threonine (thr), cysteine (cys), tyrosine (tyr), asparagine (asp), glutamic acid (glu), lysine (lys), arginine (arg), histidine (his), norleucine (nor), and modified forms thereof. Preferably, for di-leucyl containing trimers, the third amino acid component of the trimer is one of the following: leucine (leu), valine (val), isoleucine (isoleu), tryptophan (try) alanine (ala), methionine (met), phenylalanine (phe), tyrosine (tyr), histidine (his), and proline (pro). Exemplary trimers for use in the invention include but are not limited to the following: leu-leu-gly, leu-leu-ala, leu-leu-val, leu-leu-leu, leu-leu-ile, leu-leu-met, leu-leu-pro, leu-leu-phe, leu-leu-trp, leu-leu-ser, leu-leu-thr, leu-leu-cys, leu-leu-tyr, leu-leu-asp, leu-leu-glu, leu-leu-lys, leu-leu-arg, leu-leu-his, leu-leu-nor, leu-gly-leu, leu-ala-leu, leu-val-leu, leu-ile-leu, leu-met-leu, leu-pro-leu, leu-phe-leu, leu-trp-leu, leu-ser-leu, leu-thr-leu, leu-cys-leu, leu-try-leu, leu-asp-leu, leu-glu-leu, leu-lys-leu, leu-arg-leu, leu-his-leu, and leu-nor-leu. Particularly preferred peptides are dileucine and trileucine.

Although less preferred due to their limited solubility in water, additional dispersibility enhancing peptides for use in the invention are 4-mers and 5-mers containing two or more leucine residues. The leucine residues may occupy any position within the peptide, and the remaining (i.e., non-leucyl) amino acids positions are occupied by any amino acid as described above, provided that the resulting 4-mer or 5-mer has a solubility in water of at least about 1 mg/ml. Preferably, the non-leucyl amino acids in a 4-mer or 5-mer are hydrophilic amino acids such as lysine, to thereby increase the solubility of the peptide in water.

Also preferred are di- and tripeptides having a glass transition temperature greater than about 40° C.

Preferred di- and tripeptides for use in the present invention are those peptides that are surface active. As can be seen from the surface tension data in Example 1, dileucine and trileucine are extremely effective, even when present in low concentrations, at significantly depressing the surface tension of water. Moreover, in examining the surface tension results in Table 5 (extrapolated values), it can be seen that dipeptides and tripeptides containing two or more leucines have a much greater surface activity than dipeptides and tripeptides composed of fewer than two leucyl residues. Due to their highly surface active nature, the di- and tripeptides of the invention, when contained in dry powder compositions, tend to concentrate on the surface of the powder particles, thereby imparting to the resulting particles high dispersivities. This feature of the powders, i.e., a surface enriched with the di- or tripeptide, is illustrated by the ESCA data provided in Example 9.

Surprisingly, the addition of the representative tripeptide, trileucine, to a calcitonin formulation was effective to nearly double the ED value of the resulting powder (Example 4). This result is surprising because calcitonin itself is a surface active protein. Thus, the incorporation of another surface active material such as trileucine was not expected to significantly improve the dispersivity of the composition. Results in contrast to this expectation indicated that surface activity alone is not sufficient to significantly increase dispersibility, and further demonstrated the unusual and beneficial properties of the leucyl-containing peptides of the invention, particularly in enhancing aerosol performance.

Generally, the compositions of the invention will contain from about 1% to about 99% by weight di- or tripeptide, preferably from about 2% to about 75% by weight di- or tripeptide, and even more preferably from about 5% to about 50% by weight di- or tripeptide. Typically, the optimal amount of di- or tripeptide is determined experimentally, i.e., by preparing compositions containing varying amounts of di- or tripeptide (ranging from low to high), examining the dispersibilities of the resulting compositions as described herein, and further exploring the range at which optimal aerosol performance is attained. Such methods were employed in several of the Examples (Example 3, Example 4, Example 5, Example 6). Generally, for trileucine containing dry powder formulations, an optimal amount of trileucine appears to be around 22-25% by weight.

C. Additional Carriers and Excipients

In addition to the active agent and di- or tripeptide, compositions of the invention may optionally include one or more pharmaceutical excipients which are suitable for pulmonary administration. These excipients, if present, are generally present in the composition in amounts ranging from about 0.01% to about 95% percent by weight, preferably from about 0.5 to about 80%, and more preferably from about 1 to about 60% by weight. Preferably, such excipients will, in part, serve to further improve the features of the active agent composition, e.g., by providing more efficient and reproducible delivery of the active agent, improving the handling characteristics of powders (e.g., flowability and consistency), and/or facilitating manufacturing and filling of unit dosage forms. In particular, excipient materials can often function to further improve the physical and chemical stability of the active agent, minimize the residual moisture content and hinder moisture uptake, and to enhance particle size, degree of aggregation, particle surface properties (i.e., rugosity), ease of inhalation, and the targeting of particles to the lung. The excipient(s) may also serve simply as bulking agents when it is desired to reduce the concentration of active agent in the formulation.

Pharmaceutical excipients and additives useful in the present composition include but are not limited to amino acids, peptides, proteins, non-biological polymers, biological polymers, carbohydrates (e.g., sugars, derivatized sugars such as alditols, aldonic acids, esterified sugars, and sugar polymers), which may be present singly or in combination. Suitable excipients are those provided in Inhale Therapeutic Systems' International Publication No. WO 96/32096. Also preferred are excipients having glass transition temperatures (Tg), above about 35° C., preferably above about 40° C., more preferably above 45° C., most preferably above about 55° C.

Exemplary protein excipients include albumins such as human serum albumin (HSA), recombinant human albumin (rHA), gelatin, casein, hemoglobin, and the like. Suitable amino acids (outside of the dileucyl-peptides of the invention), which may also function in a buffering capacity, include alanine, glycine, arginine, betaine, histidine, glutamic acid, aspartic acid, cysteine, lysine, leucine, isoleucine, valine, methionine, phenylalanine, aspartame, tyrosine, tryptophan, and the like. Preferred are amino acids and polypeptides that function as dispersing agents. Amino acids falling into this category include hydrophobic amino acids such as leucine, valine, isoleucine, tryptophan, alanine, methionine, phenylalanine, tyrosine, histidine, and proline. Dispersibility-enhancing peptide excipients include dimers, trimers, tetramers, and pentamers comprising one or more hydrophobic amino acid components such as those described above.

Carbohydrate excipients suitable for use in the invention include, for example, monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), pyranosyl sorbitol, myoinositol and the like.

The compositions may also include a buffer or a pH adjusting agent, typically a salt prepared from an organic acid or base. Representative buffers include organic acid salts of citric acid, ascorbic acid, gluconic acid, carbonic acid, tartaric acid, succinic acid, acetic acid, or phthalic acid, Tris, tromethamine hydrochloride, or phosphate buffers.

The compositions of the invention may also include polymeric excipients/additives, e.g., polyvinylpyrrolidones, derivatized celluloses such as hydroxymethylcellulose, hydroxyethylcellulose, and hydroxypropylmethylcellulose, Ficolls (a polymeric sugar), hydroxyethylstarch, dextrates (e.g., cyclodextrins, such as 2-hydroxypropyl-β-cyclodextrin and sulfobutylether-β-cyclodextrin), polyethylene glycols, and pectin.

The compositions may further include flavoring agents, taste-masking agents, inorganic salts (e.g., sodium chloride), antimicrobial agents (e.g., benzalkonium chloride), sweeteners, antioxidants, antistatic agents, surfactants (e.g., polysorbates such as "TWEEN 20" and "TWEEN 80"), sorbitan esters, lipids (e.g., phospholipids such as lecithin and other phosphatidylcholines, phosphatidylethanolamines), fatty acids and fatty esters, steroids (e.g., cholesterol), and chelating agents (e.g., EDTA, zinc and other such suitable cations). Other pharmaceutical excipients and/or additives suitable for use in the compositions according to the invention are listed in "Remington: The Science & Practice of Pharmacy", $19^{th}$ ed., Williams & Williams, (1995), and in the "Physician's Desk Reference", $52^{nd}$ ed., Medical Economics, Montvale, N.J. (1998).

III. Formulation Types

The compositions described herein may be in powdered form or may be flowable liquids. Liquid formulations are preferably solutions in which the active drug is dissolved in a solvent (e.g., water, ethanol, ethanol-water, saline) and less preferably are colloidal suspensions. The liquid formulation may also be a solution or suspension of the active agent in a low boiling point propellant.

Liquid formulations containing the disclosed dileucyl-containing peptides are also highly dispersible, possessing high ED values.

IV. Preparing Dry Powders

Dry powder formulations are preferably prepared by spray drying. Spray drying of the formulations is carried out, for example, as described generally in the "Spray Drying Handbook", $5^{th}$ ed., K. Masters, John Wiley & Sons, Inc., NY, N.Y. (1991), and in Platz, R., et al., International Patent Publication No. WO 97/41833 (1997), the contents of which are incorporated herein by reference.

Active agents having a solubility in water of at least about 0.10 mg/ml (e.g., peptides, proteins, nucleotides and the like) can be sprayed dried from an aqueous solution. Utilizing this approach, the active agent is first dissolved in water, optionally containing a physiologically acceptable buffer. The pH range of active agent-containing solutions is generally between about 4 and 11, with nearer neutral pHs being preferred, since such pHs may aid in maintaining the physiological compatibility of the powder after dissolution of powder within the lung. The aqueous formulation may optionally contain additional water-miscible solvents, such as acetone, alcohols and the like. Representative alcohols are lower alcohols such as methanol, ethanol, propanol, isopropanol, and the like. The pre-spray dried solutions will generally contain solids dissolved at a concentration from 0.01% (weight/volume) to about 20% (weight/volume), usually from 0.1% to 3% (weight/volume).

The solutions are then spray dried in a conventional spray drier, such as those available from commercial suppliers such as Niro A/S (Denmark), Buchi (Switzerland) and the like, resulting in a dispersible, dry powder. Optimal conditions for spray drying the solutions will vary depending upon the formulation components, and are generally determined experimentally. The gas used to spray dry the material is typically air, although inert gases such as nitrogen or argon are also suitable. Moreover, the temperature of both the inlet and outlet of the gas used to dry the sprayed material is such that it does not cause decomposition of the active agent in the sprayed material. Such temperatures are typically determined experimentally, although generally, the inlet temperature will range from about 50° C. to about 200° C. while the outlet temperature will range from about 30° C. to about 150° C.

Variations of the above are utilized for spray-drying formulations where the active agent is a hydrophobic drug. One such process is described in Gordon, M. S., Lord, J. D., U.S. Pat. No. 5,985,248, assigned to Inhale Therapeutics Systems. In this method, a hydrophobic drug is dissolved in an organic solvent or co-solvent system, and the hydrophilic components (e.g., the leucyl-containing peptides and optional other excipients) are at least partially dissolved in the same organic solvent or co-solvent system. The resulting solution is then spray-dried to form particles. Typically, the solubility of the active agent and the hydrophilic component will govern the selection of the organic solvent system. The organic solvent is selected to provide a solubility for the hydrophilic component of at least 1 mg/ml, and preferably at least 5 mg/ml, and a solubility for the hydrophobic drug of at least 0.01 mg/ml, preferably at least 0.05 mg/ml.

Alternatively, the composition may be prepared by spray-drying a suspension, as described in Gordon, M. S., U.S. Pat. No. 5,976,574, assigned to Inhale Therapeutic Systems. In this method, the hydrophobic drug is dissolved in an organic solvent, e.g., methanol, ethanol, isopropanol, acetone, heptane, hexane chloroform, ether, followed by suspension of the hydrophilic excipient in the organic solvent to form a suspension. The suspension is then spray-dried to form particles. Preferred solvents, for both of the above spray-drying methods include alcohols, ethers, ketones, hydrocarbons, polar aprotic solvents, and mixtures thereof.

The dry powders of the invention may also be prepared by combining aqueous solutions or suspensions of the formulation components and spray-drying them simultaneously in a spray-dryer, as described in Gordon, M., U.S. Pat. No. 6,001,336, assigned to Inhale Therapeutics Systems. Alternatively, the dry powders may be prepared by preparing an aqueous solution of a hydrophilic excipient or additive, preparing an organic solution of a hydrophobic drug, and spray drying the aqueous solution and the organic solution simultaneously through a nozzle, e.g., a coaxial nozzle, to form a dry powder, as described in Gordon, M., et al, International Publication Number WO 98/29096.

Alternatively, powders may be prepared by lyophilization, vacuum drying, spray freeze drying, super critical fluid processing, air drying, or other forms of evaporative drying. In some instances, it may be desirable to provide the dry powder formulation in a form that possesses improved handling/processing characteristics, e.g., reduced static, better flowability, low caking, and the like, by preparing compositions composed of fine particle aggregates, that is, aggregates or agglomerates of the above-described dry powder particles, where the aggregates are readily broken back down to the fine powder components for pulmonary delivery, as described, e.g., in Johnson, K., et al., U.S. Pat. No. 5,654,007, 1997, incorporated herein by reference.

In another approach, dry powders may be prepared by agglomerating the powder components, sieving the materials to obtain agglomerates, spheronizing to provide a more spherical agglomerate, and sizing to obtain a uniformly-sized product, as described, e.g., and in Ahlneck, C., et al., International PCT Publication No. WO 95/09616, 1995, incorporated herein by reference.

Dry powders may also be prepared by blending, grinding, sieving or jet milling formulation components in dry powder form.

Once formed, the dry powder compositions are preferably maintained under dry (i.e., relatively low humidity) conditions during manufacture, processing, and storage. Irrespective of the drying process employed, the process will preferably result in respirable, highly dispersible particles comprising an active agent and a dileucyl-containing dimer or trimer.

V. Features of Dry Powder Formulations

Powders of the invention are further characterized by several features, most notably, (i) consistently high dispersivities, which are maintained, even upon storage (Example 8), (ii) small aerodynamic particles sizes (MMADs), (iii) improved fine particle dose values, i.e., powders having a higher percentage of particles sized less than 3.3 microns MMAD, all of which contribute to the improved ability of the powder to penetrate to the tissues of the lower respiratory tract (i.e., the alveoli) for either localized or systemic treatment. These physical characteristics of the di-leucyl peptide-containing dry powders, to be described more fully below, are important in maximizing the efficiency of aerosolized delivery of such powders to the deep lung.

Dry powders of the invention are composed of aerosolizable particles effective to penetrate into the lungs. The particles of the invention have a mass median diameter (MMD) of less than about 20 µm, preferably less than about 10 µm, more preferably less than about 7.5 µm, and most preferably less than about 4 µm, and usually are in the range of 0.1 µm to 5 µm in diameter. Preferred powders are composed of particles having an MMD from about 0.2 to 4.0 µm. In some cases, the powder will also contain non-respirable carrier particles such as lactose, where the non-respirable particles are typically greater than about 40 microns in size.

The powders of the invention are further characterized by an aerosol particle size distribution less than about 10 µm mass median aerodynamic diameter (MMAD), and preferably less than 4.0 µm. The mass median aerodynamic diameters of the powders will characteristically range from about 0.1-10 µm, preferably from about 0.2-5.0 µm MMAD, more preferably from about 1.0-4.0 µm MMAD, and even more preferably from about 1.5 to 3.5 µm. Illustrative MMAD values for exemplary di-leucyl-peptide-containing powder compositions are provided in Examples 2, 3, 4, 5, and 6. Several of these examples demonstrate an improvement in aerosol particle size distribution achieved upon incorporation of a di-leucyl di- or tripeptide into the formulation.

The powders of the invention may further be characterized by their densities. The powder will generally possess a bulk density from about 0.1 to 10 g/cubic centimeter, preferably from about 0.1-2 g/cubic centimeter, and more preferably from about 0.15-1.5 g/cubic centimeter.

The powders will generally have a moisture content below about 20% by weight, usually below about 10% by weight, and preferably below about 6% by weight. Such low moisture-containing solids tend to exhibit a greater stability upon packaging and storage.

One of the most striking features of the compositions of the invention is their dispersibility, as indicated by the ED value. The presence of the di-leucyl peptide in the formulations is effective to provide formulations having significantly improved dispersibilities. Generally, the emitted dose (ED) of these powders is greater than 30%, and usually greater than 40%. More preferably, the ED of the powders of the invention is greater than 50%, and is often greater than 55%. In fact, in looking at the Examples, di-leucyl-peptide containing powders typically possess optimized ED values as high as 80% or above. Moreover, the Examples further illustrate that the incorporation of a di-leucyl di- or tripeptide into a variety of active agent formulations was effective, in all cases, to increase the ED value of the resultant compositions, and in some instances, as much as doubling its value. Moreover, this effect was observed for both protein and small molecule active agent powders.

An additional measure for characterizing the overall aerosol performance of a dry powder is the fine particle dose (FPD), which describes the percentage of powder having an aerodynamic diameter less than 3.3 microns. The powders of the invention are particularly well suited for pulmonary delivery, and possess FPF values ranging from about 35%-85%. Such powders contain at least about 35 percent of aerosol particle sizes below 3.3 µm to about 0.5 µm and are thus extremely effective when delivered in aerosolized form, in reaching the regions of the lung, including the alveoli.

The compositions described herein also possess good stability with respect to both chemical stability and physical stability, i.e., aerosol performance, over time (Example 8). Generally, with respect to chemical stability, the active agent contained in the formulation will degrade by no more than about 10% over a time course of three months, preferably by no more than about 7%, and more preferably by no more than 5%, upon storage of the composition under ambient conditions. As illustrated by the exemplary PTH formulation in Example 8, storage under accelerated stability conditions (40° C., ambient humidity) for over a period of 3 months (12 weeks) resulted in the degradation of only 2.3% protein (from an initial value of 97.1% purity to 94.8% purity). Since accelerated temperatures result in an increase in reaction rate, one can conclude that storage of the same composition under ambient conditions would result in a degradation rate less than 2.3%, further pointing to the chemical stability of the present compositions.

With respect to aerosol performance, compositions of the invention are generally characterized by a drop in emitted dose of no more than about 20%, preferably no more than about 15%, and more preferably by no more than about 10%, when stored under ambient conditions for a period of three months. In looking at the results in Example 8, an exemplary PTH-trileucine formulation exhibited essentially no change, and in particular, no diminishment, in aerosol properties (MMAD, FPD, ED) upon storage under accelerated stability conditions (40° C., ambient humidity).

Another preferred feature of particulate compositions of the invention is an enrichment of the di-leucyl di- or tripeptide on the surface of the particles, as indicated by the results in Example 9.

The improvement in aerosol properties discovered for di-leucyl di- and tripeptide-containing composition (i.e., greatly enhanced dispersibilities, reduced fine particle dose values, smaller aerodynamic diameters), can result in several related advantages, such as: (i) reducing costly drug loses to the inhalation device, since more powder is aerosolized and is therefore available for inhalation by a subject; (ii) reducing the amount of dry powder required per unit dose, due to the high efficiency of aerosolization of powder, (iii) reducing the number of inhalations per day by increasing the amount of aerosolized drug reaching the lungs of a subject.

VI. Administration of the Composition

The formulations described herein may be delivered using any suitable dry powder inhaler (DPI), i.e., an inhaler device that utilizes the patient's inhaled breath as a vehicle to transport the dry powder drug to the lungs. Preferred are Inhale Therapeutic Systems' dry powder inhalation devices as described in Patton, J. S., et al., U.S. Pat. No. 5,458,135 (1995) Smith, A. E., et al., U.S. Pat. No. 5,740,794 (1998); and in Smith, A. E., et. al., U.S. Pat. No. 5,785,049 (1998), herein incorporated by reference.

When administered using a device of this type, the powder is contained in a receptacle having a puncturable lid or other access surface, preferably a blister package or cartridge, where the receptable may contain a single dosage unit or multiple dosage units. Convenient methods for filling large numbers of cavities (i.e., unit dose packages) with metered doses of dry powder medicament are described, e.g., in Parks, D. J., et al., WO 97/41031 (1997) incorporated herein by reference.

Also suitable for delivering the powders described herein are dry powder inhalers of the type described, for example, in Cocozza, S., et al., U.S. Pat. No. 3,906,950 (1974), and in Cocozza, S., et al., U.S. Pat. No. 4,013,075 (1997), incorporated herein by reference, wherein a premeasured dose of dry powder for delivery to a subject is contained within a hard gelatin capsule.

Other dry powder dispersion devices for pulmonarily administering dry powders include those described, for example, in Newell, R. E., et al, European Patent No. EP 129985 (1988); in Hodson, P. D., et al, European Patent No.

EP 472598 (1996); in Cocozza, S., et al., European Patent No. EP 467172 (1994), and in Lloyd, L. J. et al., U.S. Pat. No. 5,522,385 (1996), incorporated herein by reference. Also suitable for delivering the dry powders of the invention are inhalation devices such as the Astra-Draco "TURBU-HALER". This type of device is described in detail in Virtanen, R., U.S. Pat. No. 4,668,281 (1987); in Wetterlin, K., et al U.S. Pat. No. 4,667,668 (1987); and in Wetterlin, K., et al. U.S. Pat. No. 4,805,811 (1989), all of which are incorporated herein by reference. Other suitable devices include dry powder inhalers such as the Rotahaler® (Glaxo), Discus® (Glaxo), Spiros™ inhaler (Dura Pharmaceuticals), and the Spinhaler® (Fisons). Also suitable are devices which employ the use of a piston to provide air for either entraining powdered medicament, lifting medicament from a carrier screen by passing air through the screen, or mixing air with powder medicament in a mixing chamber with subsequent introduction of the powder to the patient through the mouthpiece of the device, such as described in Mulhauser, P., et al, U.S. Pat. No. 5,388,572 (1997), incorporated herein by reference.

Dry powders may also be delivered using a pressurized, metered dose inhaler (MDI), e.g., the Ventolin® metered dose inhaler, containing a solution or suspension of drug in a pharmaceutically inert liquid propellant, e.g., a chlorofluorocarbon or fluorocarbon, as described in Laube, et al., U.S. Pat. No. 5,320,094 (1994), and in Rubsamen, R. M., et al, U.S. Pat. No. 5,672,581 (1994), both incorporated herein by reference. Alternatively, the powders described herein may be dissolved or suspended in a solvent, e.g., water, ethanol, or saline, and administered by nebulization. Nebulizers for delivering an aerosolized solution include the AERx™ (Aradigm), the Ultravent® (Mallinkrodt), and the Acorn II® (Marquest Medical Products).

Prior to use, dry powders are generally stored under ambient conditions, and preferably are stored at temperatures at or below about 25° C., and relative humidities (RH) ranging from about 30 to 60%. More preferred relative humidity conditions, e.g., less than about 30%, may be achieved by the incorporation of a dessicating agent in the secondary packaging of the dosage form.

VII. Utility

The compositions of the invention are useful, when administered pulmonarily in a therapeutically effective amount to a mammalian subject, for treating or preventing any condition responsive to the administration of an active agent as described in section II.A above.

The following examples are illustrative of the present invention, and are not to be construed as limiting the scope of the invention. Variations and equivalents of this example will be apparent to those of skill in the art in light of the present disclosure, the drawings and the claims herein.

All articles, books, patents and other publications referenced herein are hereby incorporated by reference in their entirety.

EXAMPLES

Materials and Methods

A. Materials.
Ciprofloxacin Hydrochloride (Neuland Laboratories, India).
Gentamicin Sulfate (H&A (Canada) Industrial)
Netilmicin Sulfate (Scientific Instruments And Technology)
L-Leucine (Aldrich, St. Louis, Mo.)
Hydrochloric Acid (J. T. Baker, Phillipsburg, N.J.)
Sodium Hydroxide 0.1N Volumetric Solution (J. T. Baker, Phillipsburg, N.J.)
Ethanol, 200 proof (USP/NF, Spectrum Chemical Mfg. Corp., New Brunswick, N.J.)
Methanol (HPLC grade, EM Industries, Gibbstown, N.J.)
S. calcitonin (Bachem California Inc, USA Torrance, Calif.).
Trileucine (Bachem California Inc, USA Torrance, Calif.).
Other amino acids used in surface tension experiments were obtained from Sigma St. Louis, Mo.

B. Methods.
Particle Size Measurements (Horiba)

Mass median diameters (MMD) of the powders were measured using a Horiba CAPA-700 particle size analyzer (Horiba Instruments inc., Irvine, Calif.). Measurements were based upon centrifugal sedimentation of dispersed particles in suspending medium. Mass median diameter, which is based on the particle's Stokes' diameter, was calculated using the particle density and the density and viscosity of the suspending medium.

The density of the powder was set as 1.5 g/cm$^3$ for all powders. (This nominal value was used for all powders analyzed and is within a range that is typical for spray dried powders). Particle size measurements were conducted with about 5-10 mg powder suspended in 5 ml Sedisperse A-11 (Micromeritics, Norcross, Ga.) and dispersed by sonication for 10 minutes. The range over which particle size data was gathered was set to 0.4 to 10.0 μm.

Aerodynamic Particle Size Measurements

Andersen Cascade Impactor. An Andersen cascade impactor (a sieve-like apparatus with a series of stages that capture particles on plates by inertial impaction according to their size) was used to determine the MMAD and particle size distribution of aerosolized powder formulations in an air stream. The plates were weighed before and after testing and the mass of powder deposited on the plate of each stage was determined. Unless otherwise indicated, studies were undertaken using a traditional Andersen cascade impactor having eight stages (from top to bottom stages 0 to 7) with cut-off sizes ranging from 9.0 to 0.4 μm, and a final filter stage that traps particles <0.4 μm when operated at a flow rate of 28.3 L/min. The device test set-up was similar to the ED test, except that the cascade impactor and a USP (United States Pharmacopia) throat (USP 23, chapter <601>) were attached to the device mouthpiece rather than to a filter. Multiple dispersions were typically conducted for each cascade impaction run to achieve gravimetrically accurate data.

Andersen Short Stack (SS) Method. In the SS method, the order in which the stages were placed were altered from the conventional Andersen cascade impactor set-up as described above. From the top, stage 0 was utilized for inlet cone attachment to connect the throat. Stage 3 was positioned next, beneath stage 0, followed by the filter stage (stage F). The powder-containing airstream passes only through stages 0 and 3; air (but not powder) flows through the other stages, which are placed under stage F to hold the remainder of the assembly in place. A pre-weighed filter was placed on stage F and captured particles <3.3 μm. A second filter was placed on an inverted plate under stage 3, and captured particles >3.3 μm. For the studies described herein, one BP (blister pack) containing 2 mg of powder composition was dispersed in an aerosol delivery device and a vacuum was pulled at 28.3 L/min as per USP methodology. This process was then repeated two times for a target mass of 6 mg per run. The filters were then removed and weighed to determine the amount of powder deposited.

Example 1

Surface Activity of Di- and Tripeptides

The surface tension of several representative dipeptides, tripeptides, and proteins was measured at 25° C. and 45° C. to provide an indication of their relative surface activities. Surface tension measurements were carried out using a Kruss Processor Tensiometer-K12 with the Wilhelmy-method (Plate method).

Solutions were prepared by dissolving either 0.05%, 0.2%, or 0.6% peptide/protein (by weight) along with an appropriate amount of raffinose by weight to provide final solutions having a 1.0% by weight solids content. Surface tension measurements at 25° C. and 45° C. were then obtained for the test solutions at three different time points (49 seconds, 100 seconds and 194 seconds). The results are shown in Tables 1-5 below.

Highly surface active peptides and proteins are those that are effective to lower the surface tension of water from its control value(s). As can be seen in Tables 1-4, raffinose (which was added to each of the solutions to bring the overall solids content to 1.0%) is non-surface active, and thus does not impact the surface tension results obtained for each of the peptides/proteins.

In looking at the results below, it can be seen that highly surface active peptides include the peptides, dileucine and trileucine. These peptides were as effective as the highly surface active protein, salmon calcitonin, at significantly lowering the surface tension of water. Trileucine was effective at lowering the surface tension of water to a greater extent at higher concentrations (see, for example, data for 0.05%, 0.2% and 0.6% by weight tri-leucine). In comparison to trileucine and dileucine, the dimer of isoleucine and the dimer and trimer of valine were not particularly effective at lowering the surface tension of water.

This method can be used to identify additional surface active di- and tri-peptides suitable for use in the dry powders of the invention.

TABLE 1

Surface Tension Measurements

| SAMPLE | ST, mN/m | time, s | ST, mN/m | time, s | St, mN/m | time, s |
|---|---|---|---|---|---|---|
| water blank-1 | 72.6 | 49 | 72.6 | 100 | 72.6 | 194 |
| water blank-2 | 72.5 | 49 | 72.5 | 100 | 72.4 | 194 |
| water blank-3 | 72.5 | 49 | 72.4 | 100 | 72.4 | 194 |
| 1% raffinose-1 | 72 | 49 | 72 | 100 | 72 | 194 |
| 1% raffinose-2 | 72 | 49 | 72 | 100 | 72 | 194 |
| 1% raffinose-3 | 72 | 49 | 72 | 100 | 72 | 194 |
| 0.2% tri-alanine-1 | 72.4 | 49 | 72.4 | 100 | 72.3 | 194 |
| 0.2% tri-alanine-2 | 72.2 | 49 | 72.2 | 100 | 72.2 | 194 |
| 0.2% tri-alanine-3 | 72.3 | 49 | 72.2 | 100 | 72.2 | 194 |
| 0.2% tri-glutamate-1 | 72.1 | 49 | 72.1 | 100 | 72.1 | 194 |
| 0.2% tri-glutamate-2 | 72.4 | 49 | 72.4 | 100 | 72.4 | 194 |
| 0.2% tri-glutamate-3 | 72.4 | 49 | 72.4 | 100 | 72.3 | 194 |
| 0.2% di-alanine-1 | 72 | 49 | 72 | 100 | 71.9 | 194 |
| 0.2% di-alanine-2 | 72 | 49 | 71.9 | 100 | 71.9 | 194 |
| 0.2% di-alanine-3 | 72.1 | 49 | 72.1 | 100 | 72.1 | 194 |
| 0.2% di-leucine-1 | 58.4 | 49 | 58.1 | 100 | 57.9 | 194 |
| 0.2% di-leucine-2 | 58.7 | 49 | 58.3 | 100 | 58.2 | 194 |
| 0.2% di-leucine-3 | 60.1 | 49 | 59.8 | 100 | 59.7 | 194 |
| 0.2% tri-leucine-1 | 51 | 49 | 50.9 | 100 | 50.9 | 194 |
| 0.2% tri-leucine-2 | 51 | 49 | 50.8 | 100 | 50.7 | 194 |
| 0.2% tri-leucine-3 | 51 | 49 | 50.8 | 100 | 50.7 | 194 |
| 0.2% sal. Calcitonin-1 | 48.7 | 49 | 48.6 | 100 | 48.5 | 194 |
| 0.2% sal. calcitonin-2 | 48.4 | 49 | 48.4 | 100 | 48.4 | 194 |
| 0.2% sal. calcitonin-3 | 48.4 | 49 | 48.4 | 100 | 48.4 | 194 |

Measurements conducted at 25° C. The 0.2% (wt/vol) solutions additionally contain raffinose to form solutions having a total solids content of 1% (wt/vol).

TABLE 2

Surface Tension Measurements

| SAMPLE | ST, mN/m | time, s | ST, mN/m | time, s | St, mN/m | time, s |
|---|---|---|---|---|---|---|
| water blank-1 | 72 | 49 | 71.8 | 100 | 71.7 | 194 |
| water blank-2 | 72.2 | 49 | 72.2 | 100 | 72.2 | 194 |
| water blank-3 | 71.5 | 49 | 71.6 | 100 | 71.6 | 194 |
| 0.2% di-isoleucine-1 | 67.6 | 49 | 67.2 | 100 | 67 | 194 |
| 0.2% di-isoleucine-2 | 68 | 49 | 67.8 | 100 | 67.6 | 194 |
| 0.2% di-isoleucine-3 | 67.7 | 49 | 71.6 | 100 | 71.6 | 194 |
| 0.2% di-valine-1 | 71.7 | 49 | 71.6 | 100 | 71.6 | 194 |
| 0.2% di-valine-2 | 71.6 | 49 | 71.6 | 100 | 71.6 | 194 |
| 0.2% di-valine-3 | 71.7 | 49 | 71.6 | 100 | 71.6 | 194 |
| 0.2% tri-valine-1 | 68.8 | 49 | 68.8 | 100 | 68.8 | 194 |
| 0.2% tri-valine-2 | 68.8 | 49 | 68.7 | 100 | 68.7 | 194 |
| 0.2% tri-valine-3 | 68.7 | 49 | 68.7 | 100 | 68.7 | 194 |

Surface tension measurements conducted at 25° C.
Solutions contained 0.20% (wt/vol) of one of: di-isoleucine, di-valine, or tri-valine and 0.80% (wt/vol) raffinose.

TABLE 3

Surface Tension Measurements

| SAMPLE | ST, mN/m | time, s | ST, mN/m | time, s | St, mN/m | time, s |
|---|---|---|---|---|---|---|
| 1% raffinose (pH 4)-1 | 71.4 | 49 | 71.4 | 100 | 71.4 | 194 |
| 1% raffinose (PH 4)-2 | 71.1 | 49 | 71.1 | 100 | 71.1 | 194 |
| 1% raffinose (pH 4)-3 | 71.1 | 49 | 71.1 | 100 | 71.1 | 194 |
| 1% raffinose (pH 7)-1 | 71.1 | 49 | 71.1 | 100 | 71.1 | 194 |
| 1% raffinose (pH 7)-2 | 71.1 | 49 | 71.1 | 100 | 71.1 | 194 |
| 1% raffinose (pH 7)-3 | 71.1 | 49 | 71.1 | 100 | 71.1 | 194 |
| water blank-1 | 72.1 | 49 | 72 | 100 | 72 | 194 |
| water blank-2 | 72.2 | 49 | 72.1 | 100 | 72 | 194 |
| water blank-3 | 72.2 | 49 | 72.1 | 100 | 72 | 194 |
| 0.05% leu3 (pH 4)-1 | 59.9 | 49 | 59.8 | 100 | 59.7 | 194 |
| 0.05% leu3 (pH 4)-2 | 60.4 | 49 | 60.3 | 100 | 60.2 | 194 |
| 0.05% leu3 (pH 4)-3 | 60.4 | 49 | 60.3 | 100 | 60.2 | 194 |
| 0.2% leu3 (pH 4)-1 | 51.4 | 49 | 51.2 | 100 | 51.1 | 194 |
| 0.2% leu3 (pH 4)-2 | 51.4 | 49 | 51.3 | 100 | 51.2 | 194 |
| 0.2% leu3 (pH 4)-3 | 51.4 | 49 | 51.2 | 100 | 51.1 | 194 |
| 0.6% leu3 (pH 4)-1 | 44.2 | 49 | 44.1 | 100 | 44 | 194 |
| 0.6% leu3 (pH 4)-2 | 44.3 | 49 | 44.2 | 100 | 44.2 | 194 |
| 0.6% leu3 (pH 4)-3 | 44.2 | 49 | 44.2 | 100 | 44.1 | 194 |
| 0.05% leu3 (pH 7)-1 | 60.1 | 49 | 59.8 | 100 | 59.7 | 194 |
| 0.05% leu3 (pH 7)-2 | 60 | 49 | 59.8 | 100 | 59.7 | 194 |
| 0.05% leu3 (pH 7)-3 | 60.2 | 49 | 60 | 100 | 59.8 | 194 |
| 0.2% leu3 (pH 7)-1 | 51 | 49 | 50.8 | 100 | 50.7 | 194 |
| 0.2% leu3 (pH 7)-2 | 50.9 | 49 | 50.7 | 100 | 50.6 | 194 |
| 0.2% leu3 (pH 7)-3 | 50.7 | 49 | 50.5 | 100 | 50.4 | 194 |
| 0.6% leu3 (pH 7)-1 | 43.7 | 49 | 43.7 | 100 | 43.6 | 194 |
| 0.6% leu3 (pH 7)-2 | 43.8 | 49 | 43.7 | 100 | 43.7 | 194 |
| 0.6% leu3 (pH 7)-3 | 43.8 | 49 | 43.7 | 100 | 43.7 | 194 |
| water blank-5 | 71.7 | 49 | 71.7 | 100 | 71.6 | 194 |
| water blank-6 | 72.2 | 49 | 72.1 | 100 | 72.1 | 194 |

Surface tension measurements measured at 25° C. The trileucine formulations also contain raffinose to provide solutions having a total solids content of 1% (wt/vol).

TABLE 4

Surface Tension Measurements

| SAMPLE | ST, mN/m | time, s | ST, mN/m | time, s | St, mN/m | time, s |
|---|---|---|---|---|---|---|
| water blank-5 | 69.2 | 49 | 69.2 | 100 | 69.2 | 194 |
| 1% raffinose (pH 4)-1 | 67.9 | 49 | 68 | 100 | 68 | 194 |
| 1% raffinose (pH 4)-2 | 68.2 | 49 | 68.2 | 100 | 68.2 | 194 |
| 1% raffinose (pH 4)-3 | 68 | 49 | 68 | 100 | 68.1 | 194 |
| 1% raffinose (pH 7)-1 | 68.3 | 49 | 68.3 | 100 | 68.3 | 194 |
| 1% raffinose (pH 7)-2 | 68.4 | 49 | 68.4 | 100 | 68.4 | 194 |
| 1% raffinose (pH 7)-3 | 68.4 | 49 | 68.4 | 100 | 68.4 | 194 |

TABLE 4-continued

Surface Tension Measurements

| SAMPLE | ST, mN/m | time, s | ST, mN/m | time, s | St, mN/m | time, s |
|---|---|---|---|---|---|---|
| Leu3 formulations contain raffinose to make 1% total solids content | | | | | | |
| 0.05% leu3 (pH 4)-1 | 57.1 | 49 | 57 | 100 | 57 | 194 |
| 0.05% leu3 (pH 4)-2 | 58.1 | 49 | 57.9 | 100 | 57.8 | 194 |
| 0.05% leu3 (pH 4)-3 | 58 | 49 | 57.8 | 100 | 57.8 | 194 |
| 0.2% leu3 (pH 4)-1 | 47.9 | 49 | 47.5 | 100 | 47.4 | 194 |
| 0.2% leu3 (pH 4)-2 | 47.2 | 49 | 47.2 | 100 | 47.3 | 194 |
| 0.2% leu3 (pH 4)-3 | 47.9 | 49 | 47.3 | 100 | 47.1 | 194 |
| 0.6% leu3 (pH 4)-1 | 40.9 | 49 | 40.9 | 100 | 40.8 | 194 |
| 0.6% leu3 (pH 4)-2 | 41.1 | 49 | 41 | 100 | 40.9 | 194 |
| 0.6% leu3 (pH 4)-3 | 41.1 | 49 | 41 | 100 | 40.8 | 194 |
| 0.05% leu3 (Ph 7)-1 | 58.5 | 49 | 58.4 | 100 | 58.4 | 194 |
| 0.05% leu3 (pH 7)-2 | 58.2 | 49 | 58.2 | 100 | 58.1 | 194 |
| 0.05% leu3 (pH 7)-3 | 58.2 | 49 | 58.1 | 100 | 58.1 | 194 |
| 0.2% leu3 (pH 7)-1 | 58.5 | 49 | 58.4 | 100 | 58.4 | 194 |
| 0.2% leu3 (pH 7)-2 | 58.2 | 49 | 58.2 | 100 | 58.1 | 194 |
| 0.2% leu3 (pH 7)-3 | 58.2 | 49 | 58.1 | 100 | 58.1 | 194 |

Surface tension measurements taken at 45° C. Tri-leucine-containing formulations also contain raffinose to provide a solution having a total solids content of 1%.
Additional surface tension measurements were obtained to determine dimers and trimers for use in the invention (i.e., surface active dimers and trimers).

As can be seen from the above, surface active dimers and trimers are more effective when present at higher concentrations at lowering the surface tension of water. As an example, at a concentration of 1.20 mg/ml, the presence of trileucine was effective to lower the surface tension of water from about 72 mN/m to 42 mN/s, while at a concentration of 0.68 mg/ml, trileucine was effective at lowering the surface tension of water to about 57 mN/m.

To normalize for concentration effects, surface tension values were extrapolated to solutions having a concentration of 2 mg/ml (Table 5, columns 7 and 8). Looking first at the dimers, dileucine was more effective than any of the other dimers examined in reducing the surface tension of water. Looking at data for the trimers, leu-tyr-leu is the most surface active of the trimers. Trimers containing, in addition to two leucyl residues, a hydrophobic amino acid such as tyrosine, phenylalanine, leucine, or alanine, are more surface active than trimers containing fewer than two leucyl residues.

In summary, dimers and trimers containing two or more leucines were effective at significantly lowering the surface tension of water (e.g., leu-try-ala, leu-phe-leu, leu-leu-leu, leu-leu-ala, and the like), and are preferred for use in the compositions of the invention.

TABLE 5

Surface Tension of Representative Dimers and Trimers

| SAMPLE | concentration mg/ml | 25° C. Actual MEAN | SD | 45° C. Actual MEAN | SD | 25° C. Extrapolated Values at 2 mg/ml | 45° C. Extrapolated Values at 2 mg/ml |
|---|---|---|---|---|---|---|---|
| Dimers | | | | | | | |
| Leu-2 | 13.60 | 46.6 | 0.6 | 42.7 | 0.3 | 60.4 | 52.4 |
|  | 4.53 | 54.9 | 0.5 | 48.2 | 0.1 | | |
|  | 1.51 | 61.5 | 0.6 | 53.2 | 0.1 | | |
| Leu-Val | 8.80 | 59.1 | 0.2 | 55.7 | 0.3 | 67.2 | 62.3 |
|  | 2.93 | 65 | 0.2 | 60.4 | 0.0 | | |
|  | 0.98 | 69.2 | 0.4 | 64.2 | 0.2 | | |
| Leu-Tyr | 6.40 | 62.2 | 0.1 | 59.5 | 0.3 | 68.3 | 67.3 |
|  | 2.13 | 68.0 | 0.1 | 65.6 | 0.3 | | |
|  | 0.71 | 71.5 | 0 | 68.0 | 0.1 | | |
| Val-Leu | 7.80 | 68 | 0 | 63.5 | 0.2 | 69.8 | 65.3 |
|  | 2.60 | 69.5 | 0.1 | 65.0 | 0.2 | | |
|  | 0.87 | 70 | 0.5 | 65.5 | 0.0 | | |
| Val-Ile | 10.00 | 66.1 | 0 | 61.9 | 0.2 | 70.3 | 65.8 |
|  | 3.33 | 70.1 | 0.3 | 65.3 | 0.1 | | |
|  | 1.11 | 71.6 | 0.2 | 66.3 | 0.2 | | |
| Leu | TBD | 56.7 | 0.3 | 54.7 | 0.2 | | |
|  | | 66.3 | 0.2 | 61.4 | 0.2 | | |
| Trimers | | 70.8 | 0.2 | 64.2 | 0.0 | | |
| Leu-Tyr-Leu | 2.90 | 44.7 | 0.1 | 40.8 | 0.0 | 47.9 | 44.7 |
|  | 0.97 | 51.6 | 0.1 | 49.1 | 0.1 | | |
|  | 0.32 | 58.4 | 0.1 | 55.4 | 0.3 | | |
| Leu-Phe-Leu | 6.10 | 41.5 | 0.2 | 39.3 | 0.0 | 48.3 | 46.2 |
|  | 2.03 | 48.3 | 0 | 46.2 | 0.1 | | |
|  | 0.68 | 54.7 | 0.1 | 53.6 | 0.1 | | |
| Leu-3 | 6.10 | 42.4 | 0 | 38.9 | 0.2 | 49.7 | 46.3 |
|  | 2.03 | 49.7 | 0 | 46.3 | 0.3 | | |
|  | 0.68 | 56.9 | 0 | 52.8 | 0.6 | | |
| Leu-Leu-Ala | 6.80 | 39.9 | 0.5 | 48.4 | 0.2 | 46.6 | 49.8 |
|  | 2.27 | 43.5 | 0.8 | 48.2 | 4.3 | | |
|  | 0.76 | 60.7 | 0.4 | 58.3 | 0.5 | | |
| Ala-Val-Leu | 8.70 | 55.7 | 0.2 | 53.8 | 0.0 | 65 | 58.9 |
|  | 2.90 | 62.8 | 0.5 | 57.7 | 0.2 | | |
|  | 0.97 | 67.5 | 0.5 | 60.3 | 0.1 | | |

Example 2

Aerosol Properties of a Parathyroid Hormone (PTH)-Trileucine Dry Powder

Dry powders containing an illustrative active protein, parathyroid hormone, in combination with either leucine or trileucine, were prepared. Also prepared was a dry powder absent either leucine or trileucine, to demonstrate the notable improvement in aerosol properties upon addition of trileucine.

Representative PTH powders were prepared as follows.

A. Solution Formulation Preparation

Aqueous formulation solutions were prepared at a total solids content of 1% (w/v). The pH of each solution was determined, and solutions were then spray-dried. Table 6 lists the compositions of all pre-spray-dried PTH solutions.

B. Powder Processing: Spray Drying

Powders were produced by spray drying aqueous solutions of PTH as described in A. above using a Buchi 190 mini spray dryer (Buchi Labortechnik AG, Meierseggstrasse, Switzerland) equipped with a customized nozzle (Platz, R., et al., Inhale Therapeutic Systems' International Patent Publication No. WO 97/41833, Nov. 13, 1997) and cyclone. High collection efficiencies (yields), usually between about 50-80%, were attained.

TABLE 6

PTH Dry Powder Compositions

| Lot No. | Composition | Emitted Dose, % mean n = 10 | RSD, % | MMAD (μm) | FPD |
|---|---|---|---|---|---|
| R97190 | 30% PTH 70% mannitol | 62 | 4 | — | — |
|  | 30% PTH 70% raffinose | 66 | 9 | — | — |
| R97191 | 75% PTH 25% mannitol | 51 | 3 | — | — |
|  | 30% PTH 70% leu | 78 | — | 2.43 | 0.58 |
|  | 30% PTH 70% tri-leu | 83 | — | 2.63 | 0.45 |

In looking at the results in Table 6 (and in other tables as well), it can be seen that the addition of trileucine is effective to significantly improve the aerosol performance of the resulting powder. The aerosol performance of a PTH dry powder, as indicated by its ED value, was unexpectedly increased from 51-62% to 83% by the addition of tri-leucine to the formulation. These data illustrate a tremendous improvement in emitted dose, achieved simply by addition of the exemplary surface active tripeptide, tri-leucine to the formulation. Surprisingly, even upon correcting on a mole-to-mole basis for the number of leucine amino acids contained in trileucine (3 moles leu per mole of trileucine), trileucine is more effective than leucine, on a per weight basis, at increasing the dispersivity of dry powder compositions for delivery to the lung.

Example 3

Aerosol Properties of Albuterol-Trileucine Dry Powders

Dry powders containing the small molecule, albuterol, were prepared to examine the effects of trileucine on the dispersivity/aerosol properties of dry powders containing a non-proteinaceous active agent.

A. Solution Formulation Preparation

Formulation solutions were prepared at a total solids content of 1% (w/v). For low solids-containing solutions, raffinose was added to bring the total solids content to the above value. Table 7 lists the compositions of all pre-spray dried solutions.

37. Powder Processing: Spray Drying

Powders were produced by spray drying aqueous solutions of albuterol, surface active di- or tri-peptide, and/or other excipient(s) using a Buchi 190 mini spray dryer (Buchi Labortechnik AG, Meierseggstrasse, Switzerland) as described in Example 2 above. Characteristics of the resultant powders are provided in Tables 7 and 8 below.

TABLE 7

Albuterol Dry Powders

| Formulation | Emitted Dose, % | Tg, °C. |
|---|---|---|
| 2% albuterol 98% raffinose | 31 | 102.2 |
| 2% albuterol 5% leucine raffinose | 31 | 88.57 |
| 2% albuterol 20% leucine raffinose | 34 | 93.1 |
| 2% albuterol 60% leucine raffinose | 74 | 96.6 |
| 2% albuterol 5% trileucine raffinose | 62 | 85.3 |
| 2% albuterol 20% trileucine raffinose | 78 | 95.9 |
| 2% albuterol 60% trileucine raffinose | 82 | 88.6 |

TABLE 8

Additional Aerosol Properties of Albuterol Dry Powders

| Formulation | FPD | MMAD, microns |
|---|---|---|
| 2% albuterol 60% leucine raffinose | 0.56 | 2.43 |
| 2% albuterol 20% tri-leucine raffinose | 0.59 | 2.43 |

As can be seen from the results provided above, the addition of trileucine increased the emitted dose of albuterol dry powders from about 30% to about 80%—an improvement in dispersivity of nearly three-fold! Thus, the addition of a surface active di- or tri-peptide to an active agent dry powder can, by greatly improving the powder's dispersivity, (i) reduce costly drug loses to the inhalation device, (ii) reduce the number of required inhalations per day by increasing the amount of aerosolized drug reaching the alveoli of a patient, (iii) reduce the amount of dry powder per unit dose, due to the high efficiency of aerosolization of dry powder, and (iv) increase the ease of manufacturing unit dosage forms of powdered drug, due to increased flowability of powder.

Additionally, the addition of 60% by weight leucine was required to achieve the same level of dispersivity achieved by the addition of only 20% by weight tri-leucine. Thus, tri-leucine is much more effective than leucine in improving the aerosol performance of dry powders. Moreover, a maximum in aerosol performance is typically achieved by the addition of only from about 5-25% (wt) trileucine; quantities greater than that typically provide only incremental improvements in dispersivity.

The dispersibility-enhancing effects of tri-leucine, and other surface active di- and tri-peptides, appear to be general, and extend to not only protein powders, but to powdered formulations of a wide variety of active agents (e.g., small molecules, hormones, antibiotics, and the like), as illustrated by the Examples provided herein.

Example 4

Aerosol Properties of Salmon Calcitonin-Trileucine Dry Powders

The effects of trileucine on the aerosol performance of dry powders containing salmon calcitonin, a hormone with a molecular weight of approximately 4500 daltons, were examined.

Although salmon calcitonin is a highly surface active protein, spray-dried powders containing 5% (wt) salmon calcitonin and 95% (wt) raffinose exhibited relatively low emitted dose values (of approximately 50%). In efforts to further explore the broad applicability of adding surface active di- and tri-peptides to powder formulations to increase their dispersivity, tri-leucine was added to salmon calcitonin-containing formulations to examine its impact on the resulting powders. The ability of tri-leucine to improve the dispersibility of salmon calcitonin containing dry powders was compared to the amino acid, leucine.

Powders having the compositions indicated below were prepared as described in Examples 2 and 3 above.

TABLE 9

S. Calcitonin Dry Powders

| Formulation | Emitted Dose | FPD | Tg, ° C. |
|---|---|---|---|
| 5% s. Calcitonin 95% raffinose | 48 | 0.30 | 89.9 |
| 5% s. Calcitonin 5% leucine raffinose | 47 | 0.31 | 89.3 |
| 5% s. Calcitonin 20% leucine raffinose | 50 | 0.28 | 82.9 |
| 5% s. Calcitonin 40% leucine raffinose | 48 | 0.29 | 82.3 |
| 5% s. Calcitonin 60% leucine raffinose | 53 | 0.22 | 80.5 |
| 5% s. Calcitonin 80% leucine raffinose | 64 | 0.29 | 74.5 |
| 5% s. Calcitonin 5% tri-leucine raffinose | 58 | 0.46 | 89 |

TABLE 9-continued

S. Calcitonin Dry Powders

| Formulation | Emitted Dose | FPD | Tg, ° C. |
|---|---|---|---|
| 5% s. Calcitonin 20% tri-leucine raffinose | 72 | 0.50 | 91.1 |
| 5% s. Calcitonin 40% tri-leucine raffinose | 76 | 0.46 | 83.4 |
| 5% s. Calcitonin 60% tri-leucine raffinose | 84 | 0.49 | 94.3 |
| 5% s. Calcitonin 80% tri-leucine raffinose | 86 | 0.49 | 115.2 |

Representative mass median aerodynamic diameters were determined for two of the formulations.

TABLE 10

Mass Median Aerodynamic Diameters of Calcitonin Powders

| Formulation | MMAD |
|---|---|
| 5% s. Calcitonin 20% leucine raffinose | 3.39 |
| 5% s. Calcitonin 20% tri-leucine raffinose | 2.87 |

From the above data, it can be seen that tri-leucine can be used to improve the aerosol properties of dry powder formulations of a wide range of active agents/medicaments for aerosolized delivery to the lung.

Trileucine provided nearly a 100% improvement in the emitted dose value of a control powder containing salmon calcitonin and raffinose, nearly doubling its ED value from 48% to 86%. Moreover, tri-leucine was more effective in enhancing powder dispersibility than leucine. While a representative formulation containing 80% by weight leucine exhibited an ED value of 64%, formulations containing 60-80% tri-leucine possessed ED values from 84-86%, further indicating the superiority of tri-leucine in significantly enhancing the aerosol performance of dry powders.

Example 5

Aerosol Properties of Antibiotic-Trileucine Dry Powders

The ability of tri-leucine to improve the dispersibility of antibiotic-containing dry powders was explored.

A. Antibiotic Control Powders Absent Trileucine

Ciprofloxacin Powders. Aqueous solutions containing the components presented in Table 9 were prepared at a total solids content of 1% (w/v). The pH of each solution was determined, and solutions were then spray-dried as described in Example 2 to prepare dry powders.

TABLE 11

| Batch Number | Quantitative Composition Prior to Spray Drying[1] | | Moisture Content | MMAD (μm) | Emitted Dose |
|---|---|---|---|---|---|
| (1) 1326-16 | Ciprofloxacin hydrochloride | 1136 mg | 1.4% | 2.8 | 42% (RSD = 8) |
| | DI water | 113 ml | | | |
| | solid product: cipro | 100% | | | |
| (2) 1326-29 | Ciprofloxacin hydrochloride | 2047 mg | 3.2% | 4.5 | 51% (RSD = 7) |
| | DI water | 200 ml | | | |
| | Sodium hydroxide | QS to pH = 12 | | | |
| | solid product: cipro | 100% | | | |
| (3) 1300-MG-7 | Ciprofloxacin hydrochloride | 1995 mg | 1.2% | 2.9 | 33% (RSD = 13) |
| | Methanol | 100 ml | | | |
| | DI water | 100 ml | | | |
| | solid product: cipro | 100% | | | |

Gentilmicin, Netilmicin Powders.

Dry powder compositions containing gentamicin or netilmycin were prepared by mixing gentarmicin sulfate or netilmycin sulfate and excipient(s) (if used) with a liquid medium to form a solution. The pH of the solution was adjusted as appropriate to facilitate solubilization and/or stabilization of the components in the solution. Quantitative formulations are identified in Table 12 below. The solutions were then spray-dried as described in Example 2 above to yield dry powders. For formulations that utilized organic to solvents, a modified Buchi 190 Mini Spray Dryer was used that was supplied with nitrogen as the gas source and equipped with an oxygen sensor and other safety equipment to minimize the possibility of explosion.

TABLE 12

Gentamicin/Netilmicin Dry Powders

| Batch Number | Quantitative Composition | | Moisture Content | MMAD (μm) | Emitted Dose |
|---|---|---|---|---|---|
| 1326-31 | Gentamicin sulfate | 2076 mg | 4.1%[1] | 3.0 | 37% (RSD[3] = 6) |
| | DI water | 200 ml | | | |
| | Hydrochloric acid | QS to pH = 5 | | | |
| 1326-32 | Gentamicin sulfate | 2053 mg | 1.1%[1] | 2.4 | 40% (RSD = 14) |
| | DI water | 200 ml | | | |
| | Sodium hydroxide | QS to pH = 10 | | | |
| 1300-MG-11 | Gentamicin sulfate | 2012 mg | 4.8%[2] | 3.0 | 45% (RSD = 10) |
| | Ethanol | 40 ml | | | |
| | DI water | 160 ml | | | |
| 1300-MG-9 | Netilmicin Sulfate | 1626 mg | 4.2% | 3.2 | 47% (RSD = 8) |
| | DI water | 163 ml | | | |
| 1300-MG-14 | Netilmicin Sulfate | 1512 mg | 5.1% | 2.9 | 39% (RSD = 7) |
| | Ethanol | 30 ml | | | |
| | DI water | 120 ml | | | |

[1]Determined with Karl-Fischer reagent titrimetric method
[2]Determined with thermogravimetric analysis
[3]Relative Standard Deviation B. Trileucine-Containing Antibiotic Powders Aqueous solutions (100 ml total volume) containing antibiotic and tri-leucine at a total solids content of 1% were prepared and the pH of the solutions adjusted to pH 4. The resulting solutions were then spray-dried to produce powders having the relative amounts of antibiotic and tri-leucine indicated in Table 13 below.

TABLE 13

Antibiotic-Trileucine Dry Powders

| Formulation | Yield, % | MMAD, μm | FPD (< 3.3 μm) | ED, % |
|---|---|---|---|---|
| 95% Cipro 5% Leu-3 | 64.2 | 2.43 | 0.57 | 77.7 |
| 75% Cipro 25% Leu-3 | N.A. | 2.65 | N.A. | 83.0 |
| 45% Cipro 55% Leu-3 | 55.0 | 2.62 | 0.48 | 70.7 |
| 95% Gent. 5% Leu-3 | 61.4 | 2.15 | 0.66 | 75.7 |
| 75% Gent. 25% Leu-3 | 52.0 | 2.25 | 0.66 | 93.9 |
| 55% Gent. 45% Leu-3 | 54.2 | 2.51 | 0.51 | 87.3 |
| 95% Netil. 5% Leu-3 | 62.0 | 2.08 | 0.58 | 82.4 |

TABLE 13-continued

Antibiotic-Trileucine Dry Powders

| Formulation | Yield, % | MMAD, μm | FPD (< 3.3 μm) | ED, % |
|---|---|---|---|---|
| 75% Netil. 25% Leu-3 | 50.0 | 2.14 | 0.66 | 91.3 |
| 55% Netil. 45% Leu-3 | 40.0 | 2.73 | 0.49 | 90.4 |

As can be seen from the results in Table 13, the addition of tri-leucine was effective to notably enhance the dispersibility of powders prepared from three different antibiotic compounds from two different antibiotic classes, ciprofloxacin (a quinolone), gentamicin and netilmicin (aminoglycosides). The ED values for ciprofloxacin powders increased from values ranging from 33-51% to values ranging from 71-83%. Similar beneficial results were observed for gentamicin powders, whose ED values were improved from 37-45% to 76-94% by addition of tri-leucine, and for netilmicin, whose ED values improved from 39-47% to 82-91%. The optimal relative amount of tri-leucine was determined for each of the three antibiotic powders and determined to be approximately 25%, i.e., optimal ED values were observed for powders containing 25% by weight tri-leucine relative to antibiotic.

Example 6

Aerosol Properties of Powders Containing Interferon-β in Combination with Trileucine The broad applicability of the use of surface active di- and tri-peptides for increasing powder dispersivity was further explored in interferon-β powders. Interferon-β (a type I interferon) is a cytokine with antiviral, antiproliferative, and immunomodulatory activity.

Powders containing interferon-β and optionally tri-leucine and/or other excipients (hydroxyethylstarch, HES and raffinose) were prepared as described above. The solids content of the pre-dried solutions was 1%, with the exception of Lot No. RB27, which possessed a solids content of 0.5%. The composition of the final powders is given in Table 14 below.

TABLE 14

Interferon-β Powders Containing Tri-leucine

| Lot # | Comp. | ED, % mean (n = 10) | RSD, % | MMAD, μm | FPD, % | Yield, % | % < 5 μm, % |
|---|---|---|---|---|---|---|---|
| RB19 | 10% IFN-β 45% Leu-3 45% HES | 81 | 7 | 3.2 | 48 | 56 | 79 |
| RB21 | 10% IFN-β 45% Leu-3 45% Raff. | 80 | 6 | 2.9 | 46 | 61 | 85 |
| RB24 | 10% IFN-β 90% Leu-3 | — | — | — | — | 9* | — |
| RB27 | 10% IFN-β 67.5% Leu-3 22.5% Raff. | 74 | 4 | 2.9 | 49 | 40 | 81 |
| RB29 | 10% IFN-β 45% Leu-3 45% HES | 79 | 5 | 3.2 | 41 | 50 | 83 |
| RB36 | 10% IFN-β 22.5% Leu-3 67.5% Raff. | 87 | 3 | — | — | 61 | — |
| 99320 | 10% IFN-β 90% Raff. | 64 | — | — | — | — | — |

*No tests performed due to low yield.

As with the other active-agent containing powders, the addition of tri-leucine to powders composed of interferon-β served to increase the dispersivity and overall aerosol properties of the resulting powder. Although the improvement was not as striking in some of the previous examples. addition of tri-leucine enhanced the ED values of an interferon-β powder from 64% to 74-87%. As in the previous example, it appears that an optimal amount of tri-leucine is around about 22-25% by weight for the IFN-β powder.

Example 7

Factor IX Dry Powders

Powders containing factor IX, a 55,000 dalton glycoprotein with a modular domain structure and numerous post-translational modifications, useful in the treatment of hemophilia B, and trileucine and/or other excipient(s), were prepared to further explore the dispersivity-enhancing effects of tri-leucine and other surface active di- and tri-peptides on different medicaments.

Powders containing Factor IX, both with and without leucine or a leucine-containing dimer or trimer, were prepared as described previously. The solids content of the pre-spray-dried solution was 1% by weight (w/v). Yields of the spray dried powders ranged from 40 to 60%. The formulations of the dried powders are provided in Table 15 below.

TABLE 15

Factor IX Powders

| Formulation | Emitted Dose (RSD) | MMAD |
|---|---|---|
| 93% Factor IX/7% NaCitrate | 57 (5%) | — |
| 37% Factor IX/3% Na Citrate/60% Leucine | 78 (3%) | 2.9 |
| 56% Factor IX/4% Na Citrate/40% Trileucine | 89 (5%) | 2.7 |

The results in Table 15 further support the effectiveness of tri-leucine at significantly improving the dispersibility of dry powder compositions, irrespective of the active agent contained in the composition. Moreover, as in the previous examples, tri-leucine is better than leucine in significantly improving the dispersibility of the composition (from an ED of 57% to 89%), and can achieve such enhancement when used in smaller quantities than leucine.

Example 8

Stability Studies

The chemical and physical stability of packaged PTH powders under accelerated stability conditions were evaluated on the basis of the change in protein concentration and aerosol properties measured between initial and 3-month time points. PTH-trileucine and PTH-leucine powders were prepared as in Example 2 above.

Powders were hand-filled in blister packs (BPs). The blister packs were placed in petri dishes (20-60 BPs/dish).

TABLE 16

Accelerated stability study at 40° C./Ambient Relative Humidity

| Formulation ID Composition | Packaged Storage Condition no 2$^{nd}$ wrap no dessicant 40° C./ambient RH | % Purity (by area) | % Emitted Dose (rsd) | Fine Particle Dose (FPD) <3.3 μm | MMAD (μm) | % Wt. Change (TGA) |
|---|---|---|---|---|---|---|
| R99484 | initial | 97.0 | 79.6 (3) | 0.58 | 2.5 | 1.4 |
| 30% PTH/ | 4 weeks | n/a | 74.9 (5) | n/a | n/a | 1.7 |
| 70% Leucine | 6 weeks | n/a | 75.2 (6) | n/a | n/a | n/a |
|  | 8 weeks | 95.2* | 78.8 (6) | 0.55 | 2.4 | 2.2 |
|  | 12 weeks | n/a | 78.6 (3) | n/a | n/a | TBD |
| R99485 | initial | 97.1 | 79.4 | 0.45 | 2.9 | 2.6 |
| 30% PTH/70% | 4 weeks | n/a | 75.8 | n/a | n/a | 2.4 |
| tri-leucine | 6 weeks | n/a | 81.6 | n/a | n/a | n/a |
|  | 8 weeks | 94.8 | 81.6 | 0.44 | 2.9 | 2.4 |
|  | 12 weeks | n/a | out of BP | n/a | out of BP | out of BP |

*the chemical stability of the 8 weeks, 40° C./ambient RH sample is similar to the stability of the 6 months, 40° C./dry sample (foiled wrapped w/ desiccants) of a 30% PTH/70% mannitol formulation.

In looking at the results in Table 16, it can be seen that the trileucine-containing formulation is both chemically and physically stable upon storage, even at temperatures increased over ambient. Specifically, the 30% PTH/70% trileucine powder exhibited minimal degradation of protein over the timecourse of 3 months, while the aerosol performance of the powder remained essentially unchanged.

Example 9

Electron Spectroscopy of Chemical Analysis (ESCA) of Powder Formulations

ESCA analysis was carried out on certain powder formulations to investigate the surface enrichment of di-leucyl di- or tripeptide in the particles. The relative concentrations of powder components in the bulk powder is provided in the column, "Formulation"; the concentration of each component on the surface of the particles, as determined by ESCA, is provided in the column, "ESCA result".

TABLE 17

SCal/Raffinose/Leu formulations pH7

| Lot No. |  | Formulation (% w/w) | ESCA result (% w/w) |
|---|---|---|---|
| R99282 | sCal | 5 | 53 |
| pH7 | Leucine | 0 | — |
|  | Raffinose | 95 | 47 |
| R99283 | sCal | 5 | 11 |
| pH7 | Leucine | 5 | 52 |
|  | Raffinose | 90 | 38 |
| R99284 | sCal | 5 | 39 |
| pH7 | Leucine | 20 | 28 |
|  | Raffinose | 75 | 33 |
| R99286 | Scal | 5 | 26 |
| pH7 | Leucine | 80 | 64 |
|  | Raffinose | 15 | 9 |

TABLE 18

Leucyl-Peptide/Raffinose formulations

| Lot No. |  | Formulation (% w/w) | ESCA result (% w/w) |
|---|---|---|---|
| R99337 | Leucine-2 | 5 | 28.7 |
| pH7 | Raffinose | 95 | 71.3 |
| R99338 | Leucine-2 | 20 | 44.1 |
| pH7 | Raffinose | 80 | 55.9 |
| R99339 | Leucine-2 | 60 | 94.9 |
| pH7 | Raffinose | 40 | 5.1 |
| R99340 | Leucine-3 | 20 | 97.1 |
| pH7 | Raffinose | 80 | 2.9 |
| R99342 | Alanine-3 | 20 | 41.3 |
| pH7 | Raffinose | 80 | 58.7 |

TABLE 19

SCal/Raffinose/Leu-3 formulations pH4

| Lot No. |  | Formulation (% w/w) | ESCA result (% w/w) |
|---|---|---|---|
| R99435 | Scal | 5 | 36.6 |
| pH4 | Leucine-3 | 0 | 0 |
|  | Raffinose | 95 | 63.4 |
|  | Scal | 5 | 17.9 |
| pH4 | Leucine-3 | 5 | 7.0 |
|  | Raffinose | 90 | 75.1 |

TABLE 19-continued

SCal/Raffinose/Leu-3 formulations pH4

| Lot No. | | Formulation (% w/w) | ESCA result (% w/w) |
|---|---|---|---|
| R99437 | Scal | 5 | 46.4 |
| pH4 | Leucine-3 | 20 | 24.2 |
|  | Raffinose | 75 | 29.4 |
| R99438 | Scal | 5 | 22.7 |
| pH4 | Leucine-3 | 40 | 74.8 |
|  | Raffinose | 55 | 2.5 |
| R99439 | Scal | 5 | 16.4 |
| pH4 | Leucine-3 | 60 | 81.6 |
|  | Raffinose | 35 | 2.0 |

The above results indicate that powders containing a surface active material are enriched at the surface in concentration of surface active material. Surface enrichment of di- or trileucine is observed for both the non-active agent containing powders in Table 18 and for the s. calcitonin powders in Table 19.

Although the ESCA results for the calcitonin powders are subject to some variability (this is due to the difficulty of separating out surface concentration contributions by components having the same atom within their structures i.e., calcitonin vs. trileucine), the overall trend observed supports the finding of powders in which the surface concentration of the di-leucyl di- or tripeptide is greater than that in the bulk powder.

It is claimed:

1. A dry powder composition comprising a plurality of particles, wherein the particles comprise an active agent and a di- or tripeptide comprising at least two leucines, wherein said di- or tripeptide is present in an amount effective to increase the emitted dose of the composition over the emitted dose of the composition absent said di- or tripeptide.

2. The dry powder composition of claim 1, wherein said composition is suitable for delivery to the lung or deep lung by inhalation.

3. The composition of claim 1, comprising from about 1% by weight to about 99% by weight di- or tripeptide.

4. The composition of claim 3, comprising from about 5% to about 75% by weight di- or tripeptide.

5. The composition of claim 4, comprising from about 5% to about 50% by weight di- or tripeptide.

6. The composition of claim 1, wherein the particles further comprise a pharmaceutically acceptable excipient or carrier.

7. The composition of claim 6, wherein said excipient is selected from the group consisting of carbohydrates, amino acids, peptides, proteins, organic acid salts, and polymers.

8. The composition of claim 1 in combination with a dry powder inhaler device, wherein the dry powder composition and inhaler device combination have an emitted dose of at least about 30%.

9. The composition of claim 1 in combination with a dry powder inhaler device, wherein the dry powder composition and inhaler device have an emitted dose of at least about 45%.

10. The composition of claim 1, wherein the di- or tripeptide comprises the dipeptide dileucine.

11. The composition of claim 1, wherein the di- or tripeptide comprises a tripeptide comprising two leucines and an amino acid selected from the group consisting of leucine (leu), valine (val), isoleucine (isoleu), tryptophan (try), alanine (ala), methionine (met), phenylalanine (phe), tyrosine (tyr), histidine (his), and proline (pro).

12. The composition of claim 11, wherein said di- or tripeptide comprises trileucine.

13. The composition of claim 1, wherein the particles have an MMD of less than about 10 microns.

14. The composition of claim 1, wherein the particles have an MMD of less than about 4.0 microns.

15. The composition of claim 1, wherein the particles have an MMAD of less than about 10 microns.

16. The composition of claim 1, wherein the particles have an MMAD of less than about 4 microns.

17. The composition of claim 1, wherein the di- or tripetide possesses a glass transition temperature greater than about 40° C.

18. The dry powder composition of claim 1, wherein the dry powder composition has a drop in emitted dose of no more than about 10% when said composition is stored under ambient conditions for a period of three months.

19. The dry powder composition of claim 1, wherein the dry powder composition has a degradation of less than about 5% by weight of the active agent upon storage of said composition under ambient conditions for a period of three months.

20. The dry powder composition of claim 1, wherein said active agent is selected from the group consisting of insulin, cyclosporin, parathyroid hormone, follicle stimulating hormone, VLA-4 inhibitors, interleukin-4R, thrombopoietin, c-peptide, amylin, pro-insulin, interleukin-1, interleukin-2, alpha-1-antitrypsin, budesonide, human growth hormone, growth hormone releasing hormone, interferon alpha, interferon beta, growth colony stimulating factor, keratinocyte growth factor, glial growth factor, tumor necrosis factor, leutinizing hormone releasing hormone, calcitonin, low molecular weight heparin, somatostatin, respiratory syncytial virus antibody, erythropoietin, Factor VIII, Factor IX, ceredase, cerezyme and analogues, agonists and antagonists thereof.

21. The dry powder composition of claim 1, wherein the particles have a bulk density from 0.1 to 10 grams per cubic centimeter.

22. The dry powder composition of claim 21, wherein the particles have a bulk density from 0.5 to 2.0 grams per cubic centimeter.

23. A method for enhancing the aerosol performance of a dry powder, said method comprising:

incorporating into a liquid formulation comprising an active agent, a di- or tripeptide comprising at least two leucines, and drying said liquid formulation such that a dry powder containing particles that comprise the active agent and the di- or tripeptide is produced, whereby the resultant dry powder possesses an emitted dose that is increased over the emitted dose of a dry powder having the same components but absent said di- or tripeptide.

24. The method of claim 23, wherein the di- or tripeptide that is incorporated into the liquid formulation comprises dileucine.

25. The method of claim 23, wherein the di- or tripeptide that is incorporated into the liquid formulation comprises tri-peptide comprising two leucines and an amino acid selected from the group consisting of leucine (leu), valine (val), isoleucine (isoleu), tryptophan (try), alanine (ala), methionine (met), phenylalanine (phe), tyrosine (tyr), histidine (his), and proline (pro).

26. The method of claim 23, wherein said liquid formulation is an aqueous formulation.

27. The method of claim 23, wherein a pharmaceutically acceptable excipient or carrier is also incorporated into said liquid formulation.

28. The method of claim 23, wherein said drying step is selected from the group consisting of spray-drying, freeze-drying, and spray-freeze drying.

29. The method of claim 23, wherein the emitted dose of the dry powder is increased by at least about 5% over that of a dry powder having the same components and absent said di- or tripeptide.

30. The method of claim 29, wherein the emitted dose of the dry powder is increased by at least about 10% over that of a dry powder having the same components and absent said di- or tripeptide.

31. The method of claim 23, wherein said dry powder is characterized by an emitted dose of at least about 30%.

32. The method of claim 23, wherein said active agent is selected from the group consisting of insulin, cyclosporin, parathyroid hormone, follicle stimulating hormone, VLA-4 inhibitors, interleukin-4R, thrombopoietin, c-peptide, amylin, pro-insulin, interleukin-1, interleukin-2, alpha-1-antitrypsin, budesonide, human growth hormone, growth hormone releasing hormone, interferon alpha, interferon beta, growth colony stimulating factor, keratinocyte growth factor, glial growth factor, tumor necrosis factor, leutinizing hormone releasing hormone, calcitonin, low molecular weight heparin, somatostatin, respiratory syncytial virus antibody, erythropoietin, Factor VIII, Factor IX, ceredase, cerezyme and analogues, agonists and antagonists thereof.

33. A method for delivery of a dry powder composition to the lungs of a mammalian patient, said method comprising administering by inhalation the dry powder composition of claim 1 in aerosolized form.

34. A dry powder composition comprising a plurality of particles, wherein the particles comprise an active agent and a di- or tripeptide comprising at least two leucines, wherein the di-or tripeptide comprises the dipeptide dileucine.

35. The dry powder composition of claim 34, wherein said composition is suitable for delivery to the lung or deep lung by inhalation.

36. The composition of claim 34, wherein the particles have an MMAD of less than about 10 microns.

37. A dry powder composition comprising a plurality of particles, wherein the particles comprise an active agent and a di- or tripeptide comprising at least two leucines, wherein said di- or tripeptide comprises trileucine.

38. The dry powder composition of claim 37, wherein said composition is suitable for delivery to the lung or deep lung by inhalation.

39. The composition of claim 37, wherein the particles have an MMAD of less than about 10 microns.

* * * * *